(12) United States Patent
Giraud et al.

(10) Patent No.: US 9,040,689 B2
(45) Date of Patent: May 26, 2015

(54) COMPOUNDS USEFUL AS LIGANDS AND PARTICULARLY AS ORGANIC CHROMOPHORES FOR COMPLEXING LANTHANIDES AND APPLICATIONS THEREOF

(75) Inventors: Marion Giraud, Paris (FR); Renaud Demadrille, Saint Egreve (FR); Marinella Mazzanti, Saint Martin le Vinoux (FR); Eugen Sorin Andreiadis, Grenoble (FR)

(73) Assignee: COMMISSARIAT A L'ENERGIE ATOMIQUE, Paris (FR)

( * ) Notice: Subject to any disclaimer, the term of this patent is extended or adjusted under 35 U.S.C. 154(b) by 1179 days.

(21) Appl. No.: 12/733,675

(22) PCT Filed: Sep. 17, 2008

(86) PCT No.: PCT/EP2008/062351
§ 371 (c)(1),
(2), (4) Date: Nov. 26, 2010

(87) PCT Pub. No.: WO2009/037277
PCT Pub. Date: Mar. 26, 2009

(65) Prior Publication Data
US 2011/0112289 A1 May 12, 2011

(30) Foreign Application Priority Data
Sep. 17, 2007 (FR) .................................... 07 57640

(51) Int. Cl.
| C07D 401/04 | (2006.01) |
| C07D 401/14 | (2006.01) |
| H01L 51/00 | (2006.01) |
| C07D 409/14 | (2006.01) |
| C07F 7/08 | (2006.01) |
| H01L 51/50 | (2006.01) |

(52) U.S. Cl.
CPC .......... *H01L 51/0089* (2013.01); *C07D 401/04* (2013.01); *C07D 401/14* (2013.01); *C07D 409/14* (2013.01); *C07F 7/0814* (2013.01); *H01L 51/5016* (2013.01)

(58) Field of Classification Search
None
See application file for complete search history.

(56) References Cited

U.S. PATENT DOCUMENTS 5,639,770 A 6/1997 Chihiro et al.

FOREIGN PATENT DOCUMENTS

| EP | 1 746 094 A1 | 1/2007 |
| WO | WO 96/19459 A | 6/1996 |
| WO | WO 03/003008 A1 | 1/2003 |
| WO | WO 03/003009 A1 | 1/2003 |
| WO | WO 2005/118606 A1 | 12/2005 |
| WO | WO 2006/066968 A1 | 6/2006 |

OTHER PUBLICATIONS

Chou. Organometallics, 2007, 27, 80-87.*
Duati. Inorganic Chemistry, 2003, 42, 8377-84.*
Wu. Organometallics, 2007, 26, 2017-23.*
Andrews et al., "Gelation of La(III) cations promoted by 5-(2-pyridyl)tetrazolate and water", Chemical Communications, vol. 31, The Royal Society of Chemistry, 2006, pp. 3317-3319, XP-002486387.
Facchetti et al., "Novel Coordinating Motifs for Lanthanide(III) ions based on 5-(2-pyridyl-1-oxide)tetrazole and 5-(2-pyridyl-1-oxide)tetrazole. Potential new contrast agents", Chemical Communications, vol. 15, The Royal Society of Chemistry, 2004, pp. 1770-1771, XP-002486388.
Chan et al., "Small molecular gadolinium(III) complexes as MRI contrast agents for diagnostic imaging", Coordination Chemistry Reviews, vol. 251, No. 17-20, 2007, pp. 2428-2451, XP-002486389.
Wu et al., "Photophysical and electrochemical properties of heteroleptic tris-cyclometallated Ir(III) complexes" Polyhedron, vol. 26, No. 12, 2007, pp. 2679-2685, XP-002486390.
Wu et al., "Photophysical and Electrochemical Properties of Blue Phosphorescent Iridium(III) Complexes", Organometallics, vol. 26, No. 8, 2007, pp. 2017-2023, XP-002486391.
Lin et al., "Synthesis and Structures of 5-(pyridyl)tetrazole complexes of Mn(II)", Dalton Transactions, vol. 14, 2005, pp. 2388-2394, XP-002486392.
Yeh et al., "New dopant and host materials for blue-light-emitting phosphorescent organic electroluminescent devices", Advanced Materials, vol. 17, No. 3, 2005, pp. 285-289, XP-002486393.

(Continued)

*Primary Examiner* — Noble Jarrell
(74) *Attorney, Agent, or Firm* — Miles & Stockbridge P.C.

(57) ABSTRACT

The invention relates to the use of compounds comprising at least one 2-(1H-tetrazol-5-yl)pyridine unit, of formula (I) below:

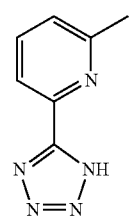

(I)

as ligands for lanthanides and, more especially, as organic chromophores for complexing these elements.
It also relates to lanthanide complexes using these compounds as complexing organic chromophores, and to new compounds containing one or more 2-(1H-tetrazol-5-yl)pyridine units, which are useful as ligands for lanthanides and, in particular, as organic chromophores for complexing these elements.
Applications: photonics and optoelectronics, especially for forming light-emitting devices such as electroluminescent diodes; biology, as for example for the preparation of luminescent probes.

12 Claims, 4 Drawing Sheets

(56) References Cited

OTHER PUBLICATIONS

Duati et al., "Enhancement of Luminescence Lifetimes of Mononuclear Ruthenium(II)-Terpyridine Complexes by Manipulation of the Sigma Donor Strength of Ligands," Inorganic Chemistry, vol. 42, No. 25, 2003, pp. 8377-8384, XP-002486394.

Andrews, et al., "Synthesis and structural characterization of cationic, neutral and hydroxo-bridged lanthanoid (La, Gd, Ho, Yb, Y) bis 5-(2-pyridyl)tetrazolate complexes", Polyhedron, vol. 26, No. 18, 2007, pp. 5406-5413, XP-002486395.

Latva et al., "Correlation between the lowest triplet state energy level of the ligand and lanthanide(III) luminescence quantum yield", Journal of Luminescence, vol. 75, 1997, pp. 149-169.

Chatterton et al., "An Efficient Design for the Rigid Assembly of Four Bidentate Chromophores in Water-Stable Highly Luminescent Lanthanide Complexes", Angewandte Chemie Int. ed., Wiley-VCH Verlag GmbH & Co. 2005, vol. 44, pp. 7595-7598.

Nonat et al., "Lanthanide Complexes of a Picolinate Ligand Derived from 1,4,7-Triazacyclononane with Potential Application in Magnetic Resonance Imaging and Time-Resolved Luminescence Imaging", Chemistry Eur. Journal, 2006, vol. 12, pp. 7133-7150.

Petoud et al., "Stable Lanthanide Luminescence Agents Highly Emissive in Aqueous Solution: Multidentate 2-Hydroxyisophthalamide Complexes of $Sm^{3+}$, $Eu^{3+}$, $Tb^{3+}$, $Dy^{3+}$", Journal of the American Chemical Society 2003, vol. 125, pp. 13324-13325.

Moore et al., "An Octadentate Luminescent Eu(III) 1,2-HOPO Chelate with Potent Aqueous Stability," Inorganic Chemistry, vol. 46, No. 14, 2007, pp. 5468-5470.

Vogtle et al., "A Dendritic Antenna for Near-Infrared Emission of $Nd^{3+}$ Ions", Chemphyschem 2001, No. 12, Wiley-VCH Verlag GmbH & Co. 2001, pp. 769-773.

Chauvin et al., "Europium and Terbium tris(Dipicolinates) as Secondary Standards for Quantum Yield Determination", Spectroscopy Letters 2004, vol. 37. No. 5, Marcel Dekker, Inc. 2004, pp. 517-532.

Mello et al., "An Improved Experimental Determination of External Photoluminescence Quantum Efficiency", Advanced Materials 1997, vol. 9, pp. 230-232.

Mukkala et al., "New Heteroaromatic Complexing Agents and Luminescence of Their Europium(III) and Terbium(III) Chelates", Helvetica Chimica Acta, vol. 75, 1992, pp. 1621-1632.

Hovinen et al., "Versatile Strategy for Oligonucleotide Derivatization. Introduction of Lanthanide(III) Chelates to Oligonucleotides", Organic Letters 2001, vol. 3, No. 16, American Chemical Society 2001, pp. 2473-2476.

Lopez et al., "Preparation and photophysical properties of precursors of inorganic macromolecules. Mono and binuclear complexes of Ru(II) and terpyridine derivatized with thiophene and 4'-(5-bromothiophene) groups", Inorganica Chimica Acta 2004, vol. 375, Elsevier B.V. 2004, pp. 3525-3531.

* cited by examiner

US 9,040,689 B2

COMPOUNDS USEFUL AS LIGANDS AND PARTICULARLY AS ORGANIC CHROMOPHORES FOR COMPLEXING LANTHANIDES AND APPLICATIONS THEREOF

TECHNICAL FIELD

The present invention relates to the use of compounds comprising at least one 2-(1H-tetrazol-5-yl)pyridine unit as ligands for lanthanides and, more especially, as organic chromophores for complexing these elements.

It likewise relates to lanthanide complexes using these compounds as complexing organic chromophores, and also to new compounds containing one or more 2-(1H-tetrazol-5-yl) pyridine units, which are useful as ligands for lanthanides and, in particular, as organic chromophores for complexing these elements.

The complexes according to the invention may find applications in numerous fields. Thus, for example, they may be used in photonics and in optoelectronics, especially for forming light-emitting devices such as electroluminescent diodes but they may also be used in biology, as for example for the preparation of luminescent probes.

BACKGROUND ART

According to the rules from the International Union of Pure and Applied Chemistry (IUPAC), the lanthanides (Ln) correspond to the series of chemical elements running from cerium (Z=58) to lutetium (Z=71).

Generally speaking, lanthanides form their most stable compounds when they are in the +3 oxidation state. The electronic structure of $Ln^{III}$ ions is that of xenon for $La^{III}$, and then corresponds to the filling of the 4f orbitals up to $[Xe] 4f^{14}$ for $Lu^{III}$.

Lanthanides are known in the literature for their luminescent properties, which may be exploited in the context of numerous applications in the fields of photonics, optoelectronics and biology (magnetic and optical imaging and labelling).

At present, the majority of studies carried out with lanthanide complexes have been aimed at establishing luminescent probes containing long-lived emitters of visible light, especially $Eu^{III}$ and $Th^{III}$, or emitters of the near-infrared spectrum, such as $Pr^{III}$, $Er^{III}$, $Yb^{III}$ or $Nd^{III}$.

Lanthanides are particularly advantageous for applications in photonics and electronics on account of their unique emission properties. This is because they exhibit very narrow emission bands, providing high purity to the colour emitted. Moreover, the life of the excited states is particularly long, and the quantum yields of luminescence are high. Furthermore, the emission ranges may be adapted, and it is possible to obtain lanthanide complexes which emit within the wavelength range from ultraviolet (UV) to near-infrared (IR).

Since the 4f-4f transitions are forbidden in accordance with the rules of Laporte, the absorption coefficient of the lanthanides is very low, and their direct excitation requires the use of high-energy laser sources.

In order to allow emission of the metal with lower energies, it is necessary to sensitize the lanthanide by complexing it with a suitable organic chromophore, which is generally a conjugated system with high absorption in the UV-visible range, such as a diketone, which is capable of absorbing photons and transferring them efficiently to the lanthanide ions. The photons which are absorbed will excite the molecule and cause it to pass into a singlet state, which is able to relax, to return to the ground state, or else to pass into a triplet state, by inter-system conversion. If the triplet state of the metal is lower, energetically speaking, than that of the chromophore, there is then a transfer of energy (by Forster or Dexter mechanism) from the triplet state of the chromophore to the triplet state of the metal, which returns to the ground state and, in so doing, emits light.

For a system of this kind to operate efficiently, in other words to have a quantum yield of luminescence that is of advantage, it is necessary for the chromophore to absorb photons and transfer them efficiently to the metal by virtue of a high compatibility of its triplet state with that of the metal.

A number of different architectures have been proposed to date for the sensitization of lanthanide ions.

In the majority of cases, the chromophores comprise pyridine, bipyridine or terpyridine units which are capable of sensitizing the emission of lanthanides which emit in the visible range. These units have been functionalized with carboxylic acid groups in the optical field, to form stable complexes with lanthanides (Latva et al., *Journal of Luminescence* 1997, 75, 149-169 [1]). Advantageous quantum yields have been obtained for the complexes formed in this way. However, their stability remains low.

It has been shown, moreover, by Chatterton et al. (*Angewandte Chemie*, International Edition in English 2005, 44, 7595-7598 [2]) and by Nonat et al. (*Chemistry, a European Journal* 2006, 12, 7133-7150 [3]) that the introduction of three picolinate groups into tripodal architectures, or of four picolinate groups into a tetrapodal architecture, is able to produce lanthanide complexes which are stable and rigid, with quantum yields that are advantageous for terbium (45-60%) but markedly lower for europium (4-7%).

2-Hydroxyisophthalamide derivatives included in tetrapodal architectures have also been found to be effective in sensitizing terbium, leading to high quantum yields for this lanthanide (50-60%), but low quantum yields, on the other hand, for europium (6%) (Petoud et al., *Journal of the American Chemical Society* 2003, 125, 13324-13325 [4]), whereas satisfactory quantum yields (of the order of 44%) have been obtained for europium by the introduction of 2-hydroxypyridones into dipodal architectures (Moore et al., *Inorganic Chemistry* 2007, 46, 5468-5470 [5]).

Furthermore, the literature does not record quantum yields of more than 0.27% for neodymium, and even this value, published by Vögtle and his colleagues (*ChemPhysChem* 2001, 2, 769-773 [6]), is an exception, the quantum yields obtained for this lanthanide being typically 0.10%.

It would therefore be desirable to have compounds available which, as well as forming complexes with the lanthanides, are capable of efficiently sensitizing a number of these lanthanides, and particularly of sensitizing europium, terbium and neodymium.

The objective set by the Inventors, therefore, was to provide such compounds.

Another objective they set was that the syntheses of these compounds and lanthanide complexes should be easy to implement and should involve only reactions that are conventionally used in organic chemistry.

Another objective they set, further, was that these compounds should make it possible to obtain stable lanthanide complexes and, as far as possible, that this stability should exist both when the complexes are in solution and when they are in the solid state.

Another objective they set, still, was that the lanthanide complexes thus obtained should, when in the solid state, exhibit excitation wavelengths that are compatible with the substrates conventionally used in optics, such as glass substrates or indium tin oxide (ITO) substrates.

Another objective they set, finally, was that the said compounds should make it possible to eliminate the presence of molecules of water in the first coordination sphere of the lanthanides, at least when the complexes are in the solid state, in order to prevent or at least reduce the non-radiative relaxation phenomena associated with the oscillation of the OH bonds.

SUMMARY OF THE INVENTION

These objectives, and others too, are achieved by the invention, which first provides for the use of a compound comprising at least one 2-(1H-tetrazol-5-yl)pyridine unit, i.e. a unit of formula (I) below:

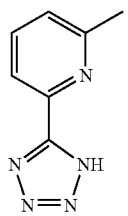

(I)

as a ligand of a lanthanide and, more especially, as an organic chromophore for complexing a lanthanide.

The compound preferably conforms to the general formula (II) below:

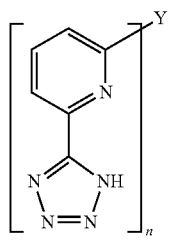

(II)

in which:

n is an integer from 1 to 5; and

Y represents the radical of an organic molecule which is bonded to the n 2-(1H-tetrazol-5-yl)pyridine unit(s).

According to a first preferred embodiment of the invention, Y represents an aromatic ring which optionally comprises one or more heteroatoms and/or one or more substituents.

In the text above and below, a "heteroatom" is any atom other than carbon or hydrogen, such as, for example, an oxygen, nitrogen, sulphur, halogen, phosphorous, boron or else silicon atom, this heteroatom being typically a nitrogen, oxygen or sulphur atom and, preferably, a nitrogen atom when it forms part of a ring, whether that ring be aromatic or not.

Moreover, although the term "substituent" must be taken, in the text above and below, in its broader accepted meaning, it is preferred for the substituents to be halogen atoms or functional groups comprising at least one heteroatom, such as, for example, —COOR', —CHO, —OR', —SR', —SCOR', —SO$_2$R', —NR'R", —CONR'R", —C(Hal)$_3$, —OC(Hal)$_3$, —C(O)Hal or —CN groups, in which R' and R" represent a hydrogen atom or an alkyl group, preferably a $C_1$ to $C_3$ alkyl group, while Hal represents a halogen atom, preferably fluorine, chlorine or bromine. One particularly preferred substituent is the carboxylic acid group.

The aromatic ring that Y may represent is preferably a substituted or unsubstituted pyridine ring, in which case n is advantageously 1 or 2 (which means that this pyridine ring is bonded to one or two 2-(1H-tetrazol-5-yl)pyridine units), or else a substituted or unsubstituted tetrazole ring, in which case n is advantageously 1 (this means that this tetrazole ring is bonded to a single 2-(1H-tetrazol-5-yl)pyridine unit).

When Y is a pyridine ring, it is preferred, on the one hand, for the carbon atoms of this ring which are situated in meta position to the nitrogen atom not to be substituted, and, on the other hand, for the 2-(1H-tetrazol-5-yl)pyridine unit(s) to which the pyridine ring is bonded to be situated in ortho and/or para position to said nitrogen atom, since this kind of configuration is particularly beneficial to the complexing of the lanthanide by the compound of general formula (II).

Accordingly, if the pyridine ring is bonded to a single 2-(1H-tetrazol-5-yl)pyridine unit, then this unit is situated, preferably, in ortho or para position to the nitrogen atom of this ring, whereas, if the pyridine ring is bonded to two 2-(1H-tetrazol-5-yl)pyridine units, then these two units are situated, preferably, in ortho position to the nitrogen atom of the pyridine ring or else one of these units is situated in ortho position and the other is situated in para position to said nitrogen atom.

With particular preference the compound conforms to the formula (III) below:

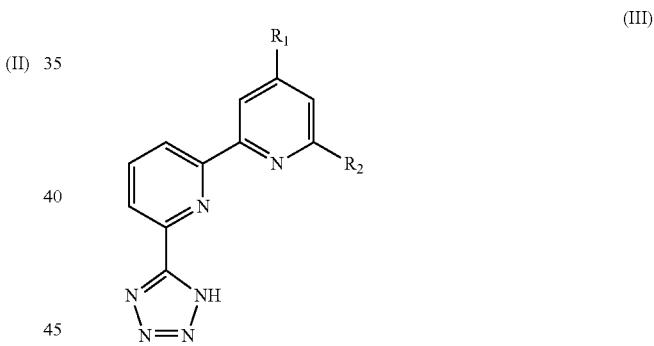

(III)

in which:

$R_1$ represents a hydrogen or halogen atom; a 5- or 6-membered aromatic ring or a sequence of two or more 5- or 6-membered aromatic rings, typically of 2 or 3 rings, bonded to one another by a covalent bond, this ring, or at least one of these rings, optionally comprising one or more heteroatoms, typically O, N or S, and/or one or more non-cyclic substituents; or else a linear or branched $C_1$ to $C_{12}$ hydrocarbon group optionally comprising one or more heteroatoms; and $R_2$ represents a carboxylic acid group; a 5- or 6-membered aromatic ring, optionally comprising one or more heteroatoms, typically O, N or S, and/or one or more non-cyclic substituents; or else a unit of formula (I) above.

In formula (III) above, $R_1$ may in particular be a phenyl or thiophene group which is optionally substituted, in particular by one or more halogen atoms, such as 4-bromophenyl or 2-bromothiophene, or else a diphenyl, dithiophene or pyridin-2-yl-phenyl group, which is optionally substituted, in particular by one or more halogen atoms or one or more $C_1$ to $C_{12}$ alkyl or $C_3$ to $C_{12}$ silylalkyl groups.

When Y is a tetrazole ring, it is preferred for this ring not to be substituted.

According to another preferred embodiment of the invention, Y represents a non-aromatic ring optionally comprising one or more heteroatoms, typically O, N or S, and/or one or more substituents, or a group of formula —$(CH_2)_p$—Z where p is an integer from 1 to 6 and Z represents an aromatic or non-aromatic ring, optionally comprising one or more heteroatoms, typically O, N or S, and/or one or more substituents.

In this embodiment, Y preferably represents a group of formula —$(CH_2)_p$—Z where p is 1 or 2 and Z is a 5- to 9-membered non-aromatic ring. This non-aromatic ring may be a 5- or 6-membered ring as is conventionally used in organic chemistry, as for example cyclopentyl, cyclohexyl, cyclopentadienyl or phenyl, but it is preferred for this ring to have a higher number of members, 9 for example, and to contain to 5 heteroatoms, advantageously nitrogen atoms, in which case this ring is preferably bonded to as many 2-(1H-tetrazol-5-yl)pyridine units as it contains heteroatoms.

Examples of such rings are the triazacyclononane and tetraazacyclononane rings.

In accordance with the invention, Y may also represent a group devoid of any ring. Thus, in particular, Y may represent a carboxylic acid group or a linear or branched $C_1$ to $C_{12}$ hydrocarbon group, this group optionally comprising one or more heteroatoms and/or one or more substituents.

Particularly preferred compounds of general formula (II) conform to the particular formulae (II-a) to (II-k) below:

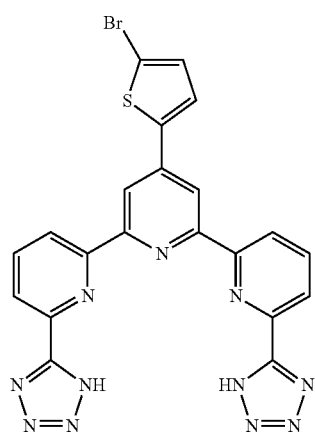

(II-a)

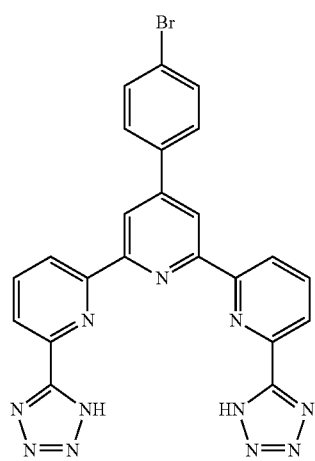

(II-b)

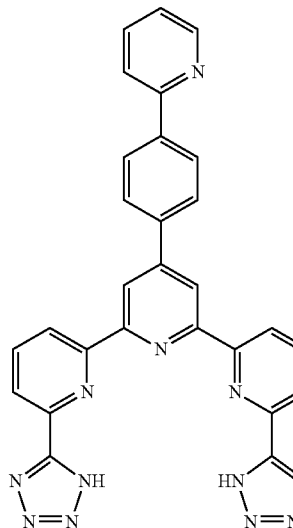

(II-c)

(II-d)

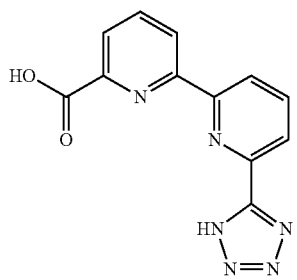

(II-e)

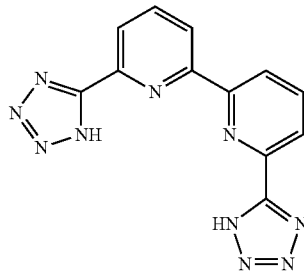

(II-f)

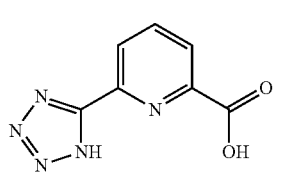

(II-g)

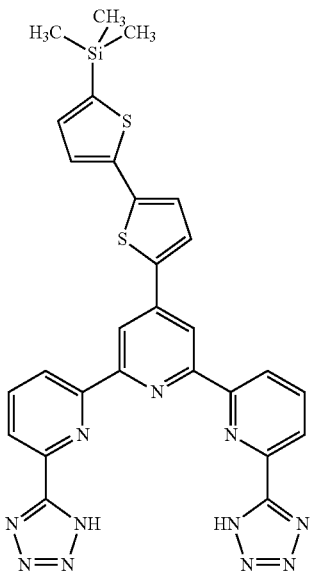

(II-h)

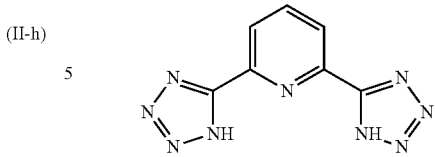

(II-i)

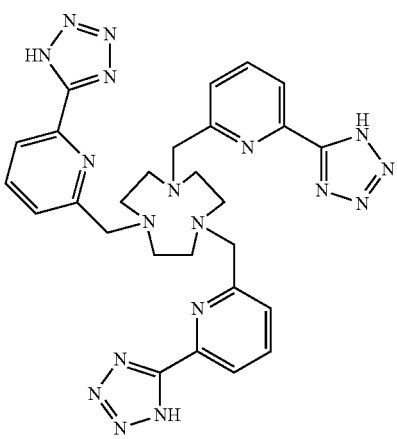

(II-j)

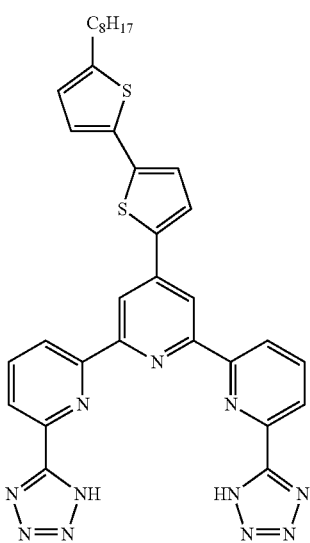

(II-k)

According to a further preferred embodiment of the invention, the lanthanide is selected from europium, terbium and neodymium.

The invention further provides a complex of a compound as defined above and a lanthanide, in which said compound acts as a complexing organic chromophore.

A complex of this kind may be represented by the formula (IV) below:

$$[Ln(COM)_m] \qquad (IV)$$

in which:
Ln represents the lanthanide;
COM represents the complexing organic chromophore; and
m is an integer corresponding to the number of molecules of the complexing organic chromophore that are bonded to the lanthanide, said number being dependent on the number of coordination sites presented by the lanthanide.

Generally speaking, the lanthanide is in the +3 oxidation state, in which case it presents 8 to 12 coordination sites and, typically, 9.

According to one preferred embodiment of the invention, the complex comprises a total of 3, 4 or 2-(1H-tetrazol-5-yl)pyridine units, bearing in mind that one unit of this type allows two coordination bonds to be formed with the lanthanide. Thus, for example, m is 2 and the complex comprises a total of 4 2-(1H-tetrazol-5-yl)pyridine units; m is 1 and the complex comprises a total of 3 2-(1H-tetrazol-5-yl)pyridine units; or else m is 4 and the complex comprises a total of 4 2-(1H-tetrazol-5-yl)pyridine units.

According to another preferred embodiment of the invention, the complex comprises, as a complexing organic chromophore, a compound which conforms either to the formula (III) shown above, in which $R_1$ and $R_2$ have the same meaning as above, or to the general formula (II) shown above in which Y represents a group of formula —$(CH_2)_p$—Z where p is 1 or 2 and Z is a 5- to 9-membered non-aromatic ring.

More specifically, the complex comprises a compound which conforms to any of the particular formulae (II-a), (II-b), (II-c), (II-d), (II-h), (II-i) and (II-j) shown above.

Moreover, the lanthanide is preferably europium, terbium or neodymium.

Among the compounds which can be used as ligands for lanthanides in accordance with the invention, some are known as chemical compounds, while others appear never to have been described in the literature.

The invention accordingly further provides a compound conforming to the general formula (II) shown above in which:
n is an integer from 1 to 5;
Y represents an aromatic or non-aromatic ring which is bonded to the n 2-(1H-tetrazol-5-yl)pyridine unit(s) and which optionally comprises one or more heteroatoms, typically O, N or S, and/or one or more substituents, or a group of formula —$(CH_2)_p$—Z where p is an integer from 1 to 6 and Z represents an aromatic or non-aromatic ring, optionally comprising one or more heteroatoms, typically O, N or S, and/or one or more substituents, this group being bonded to the n 2-(1H-tetrazol-5-yl)pyridine unit(s).

In this compound, the details concerning the ring (aromatic or non-aromatic) and the group of formula —(CH$_2$)$_p$—Z as a possible meaning of Y are as defined above. The same applies to n.

In accordance with the invention, the compound preferably conforms to any of the particular formulae (II-a), (II-b), (II-c), (II-d), (II-e), (II-f), (II-h), (II-i) and (II-j) shown above.

The invention will be appreciated more fully in light of the remainder of the description, which refers to exemplary embodiments of ligands and of complexes of lanthanides that are in accordance with the invention, and to examples which demonstrate their properties.

Of course, these examples are given only to illustrate the invention and do not in any case constitute a limitation thereon.

DETAILED DESCRIPTION OF PARTICULAR EMBODIMENTS

Figure 1:
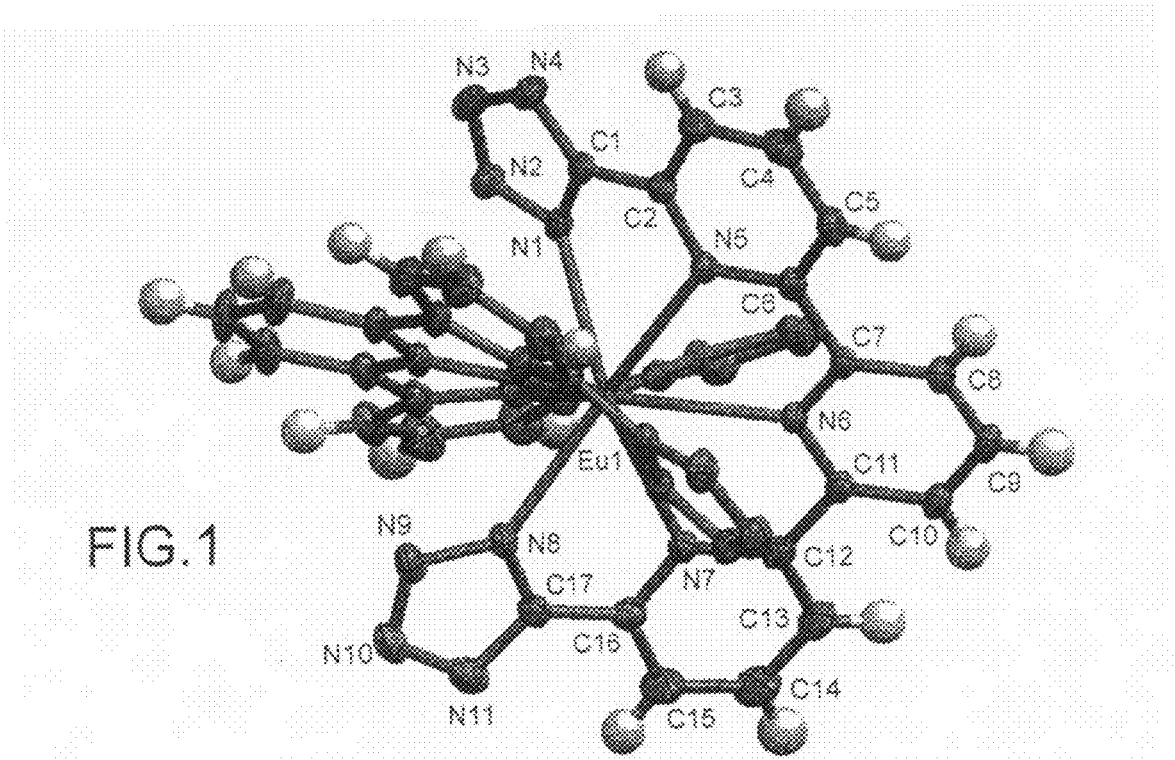
FIG. 1 shows the structure of a first complex of europium, according to the invention, as resolved by X-ray diffraction.

In the examples below, the solvents and reactants were obtained from the companies Aldrich, Fluka and Acros and were used without further purification.

The lanthanide triflates were supplied by Aldrich, and their metal content was assayed before use, in the presence of EDTA and xylene orange.

The $^1$N NMR and $^{13}$C NMR spectra were recorded on a Bruker AM-200 or Varian U-400 spectrometer and processed using the MestRe-C software, version 4.9. The complete signature of the protons in the complexes was realised using NOESY experiments (Nuclear Overhauser Effect Spectroscopy).

The elemental analyses were carried out by the "Service Central d'Analyses" (Vernaison, France).

The absorption spectra were recorded on a Varian Cary 50 UV-visible spectrophotometer. The low-resolution luminescence measurements in solution (lifetime, triplet states and quantum yields) were measured on a Perkin-Elmer LS-50B spectrometer at 298K.

For the measurements of the spectra and of the triplet states in the solid state, the spectrometer was adapted using a liquid nitrogen cooling system. The measurements of the singlet states were performed in methanol at ambient temperature, while the measurements of the triplet states were carried out in the solid state at 77K with a time of 0.2 ms. The solid-state measurements were also carried out on a Spex Horiba Jobin Yvon Fluorolog® FL 3-22 spectrometer with a double monochromator and a Hamamatsu Photonics R-928P photomultiplier.

For the measurements in the near infrared, the spectrometer was adapted with a measuring channel equipped with a FL-1004 monochromator, and the irradiation power was measured using two Jobin Yvon InGaAs detectors: one DSS-IGA020L detector (range: 800-1600 nm) cooled to 77K, and one DSS-IGA020A (range: 800-1700 nm) detector operating at ambient temperature, which is inserted into an LN2 housing comprising an elliptical mirror (90°) and coupled to a Jobin Yvon SpectrAcq2 acquisition system.

All of the spectra were corrected.

The luminescence lifetimes were measured by recording the decrease of the maximum of the spectrum, and the signal obtained is modelled by a mono-exponential function in Origin® 7.5. The values reported correspond to the average of three independent measurements. The solutions for the quantum yield measurements have an absorbance of 0.2 in a Suprasil® quartz cell with a thickness of 2 mm. The cells for the luminescence were prepared by dissolving the isolated complexes in spectroscopic-grade methanol.

The quantum yields Φ were calculated with the following equation:

$$\Phi_x/\Phi_r = A_r(\lambda) n_x^2 D_x / A_s(\lambda) n_r^2 D_r.$$

in which:
x is connected to the sample,
r is connected to the reference,
A is the absorbance at the excitation wavelength,
n is the refractive index, and
D is the emitted intensity, integrated over the whole of the spectrum.

The tris(dipicolinate) complexes [Eu(dpa)$_3^{3-}$] (Φ=24%, 7.5×10$^{-5}$ M in 0.1 M Tris buffer) and [Tb(dpa)$_3^{3-}$] (Φ=22%, 6.5×10$^{-5}$ M in 0.1 M Tris buffer) were used as references for determining the quantum yields of the europium and the terbium, respectively (Chauvin et al., *Spectroscopy Letters* 2004, 37, 517-532 [7]). The error in this type of measurement is typically considered to be 15%.

The quantum yields in the solid state were determined using the Fluorolog FL 3-22 spectrometer with a custom integrating sphere from Oriel, and with the procedure described by Mello et al. (*Advanced Materials* 1997, 9, 230-232 [8]). The spectra were corrected as a function of the instruments, using an absolute method, with an integrating sphere.

As for the X-ray crystallographic studies, all of the diffraction data were collected using a BRUKER Smart CCD diffractometer with a 3-circle detector, 2θ$_{max}$=59.38° (Mo Kα radiation, graphite monochromator, λ=0.71073 Å). In order to reduce the solvent loss, the crystals were covered with a light hydrocarbon oil and transferred into the diffractometer under nitrogen. The intensities with I>10σ (I) detected in the networks using the Bruker Sadabs program were used to refine the values of the cell parameters. The space groups were determined systematically and confirmed by resolution of the structures resolved by the direct methods, using the SHELXTL program 6.10.

EXAMPLE 1

Complexes of 2,2'-6',2"-terpyridine-6,6"-ditetrazole and various lanthanides (europium, terbium and neodymium)

1.1. Synthesis of 2,2'-6',2"-terpyridine-6,6"-ditetrazole

The title compound, referred to hereinafter as TPDTZ, which corresponds to the compound of particular formula (II-d) shown above, is synthesized starting from [2, 2'-6',2"-terpyridine]-6,6"-dicarbonitrile, referred to hereinafter as compound 1, in accordance with the following reaction scheme:

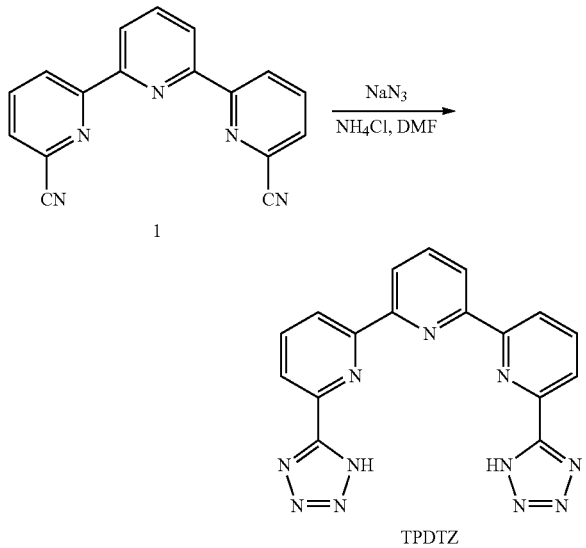

Synthesis of Compound 1

Compound 1 is synthesized as described by Mukkala et al. in *Helvetica Chimica Acta* 1992, 75, 1621-1632 [9].

Synthesis of TPDTZ

A mixture of 1.133 g (4.51 mmol) of compound 1, 1.300 g (20 mmol) of sodium azide ($NaN_3$) and 1.07 g (20 mmol) of ammonium chloride ($NH_4Cl$) in 36 ml of anhydrous dimethylformamide (DMF) is reacted under argon at 125-130° C. for 16 hours. After cooling, the inorganic salts are filtered off and the solvent is removed under reduced pressure. The residue is taken up in dilute hydrochloric acid (0.1 M, ~16 ml, pH~2-3), stirred for an hour and recovered: by filtration. The product is rinsed with cold water and dried on the filter and under vacuum.

This gives 1.505 g of TPDTZ (yield: 90%).

$^1$H NMR (200 MHz, DMSO) δ ppm: 9.29 (d, J=7.83 Hz, 2H), 9.24 (dd, J=6.65, 2.36 Hz, 2H), 8.72-8.63 (m, 5H)

$^{13}$C NMR (50 MHz, DMSO) δ ppm: 155.70, 155.29, 153.94, 144.42, 139.20, 138.60, 122.62, 122.04, 121.97.

1.2. Synthesis of C complex of TPDTZ and Europium

A suspension of 95.16 mg (0.258 mmol) of TPDTZ in 6 ml of methanol is treated with 72 μL (52.14 mg) of triethylamine (TEA) and subjected to ultrasound. Then 77.19 mg of europium triflate in 2 ml of methanol are added. The solution, which turns slightly yellow, is left at ambient temperature to crystallize. The resulting product is isolated by filtration, washed with a small volume of methanol and then of ether, and dried in the air.

This gives 66.1 mg of the complex whose structure, as resolved by X-ray diffraction, is shown in FIG. 1, in the form of yellowish white crystals (yield: 51.8%).

$^1$H NMR (400 MHz, MeOD) δ ppm: 15.51 (d, J=8.11 Hz, 2H), 12.20 (t, J=7.83, 7.83 Hz, 2H), 5.33 (d, J=7.80 Hz, 2H), 3.10 (q, J=7.32, 7.30, 7.30 Hz, 3H), 1.21 (t, J=7.31, 7.31 Hz, 4.5H) 0.72 (t, J=7.52, 7.52 Hz, 1H), −0.50 (d, J=7.59 Hz, 2H)

Elemental analysis: calculated (found) for [Eu(TPDTZ)$_2$]NHEt$_3$.1.25MeOH.1.5H$_2$O:
C: 46.92% (46.96%)
H: 4.01% (3.86%)
N: 30.51% (30.21%)
X-Ray Diffraction:
Monoclinic crystalline system
Space group C2/c
Cell Parameters:
a=16.76.4(4) Å α=90°
b=18.295(5) Å β=93.207(5)°
c=14.430(4) Å γ=90°
R indices (all data) R1=0.0360

1.3. Synthesis of a Complex of TPDTZ and Terbium

A suspension of 82.66 mg (0.224 mmol) of TPDTZ in 5 ml of methanol is treated with 62.4 μl of TEA and subjected to ultrasound. Then 67.8 mg of terbium triflate in 3 ml of methanol are added. The resulting opalescent solution is filtered and the filtrate is left at ambient temperature to crystallize. The crystals thus formed are recovered by filtration, washed with a small volume of methanol and then of ether, and dried in the air.

Partial evaporation of the mother liquor produces a second series of crystals.

Figure 2:
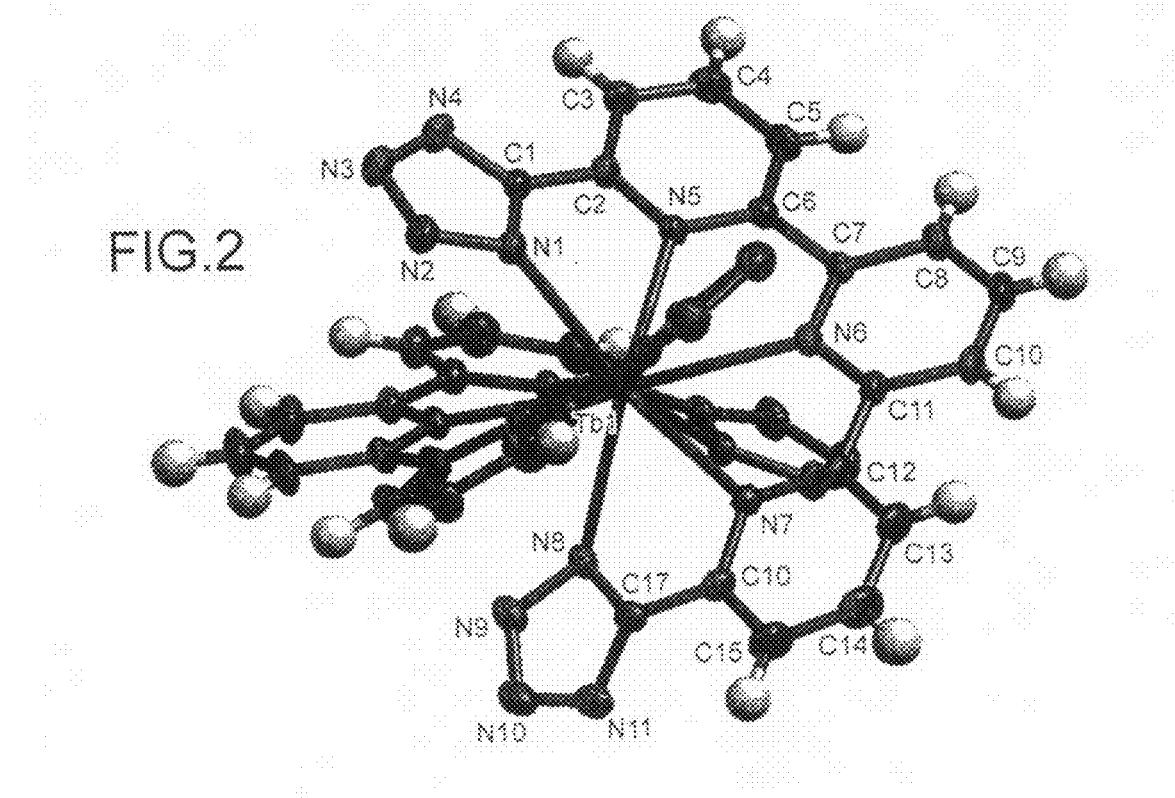
FIG. 2 shows the structure of a complex of terbium, according to the invention, as resolved by X-ray diffraction.

This gives a total of 53.6 mg of the complex whose structure, as resolved by X-ray diffraction, is shown in FIG. 2, in the form of white crystals (yield: 48%).

$^1$H NMR (400 MHz, MeOD) δ ppm: 95.43 (2H), 91.87 (1H), 4.22 (q, J=7.00, 7.00, 7.00 Hz, 3H), 2.20 (t, J=7.06, 7.06 Hz, 4.5H), −4.58 (2H), −67.59 (2H), −140.08 (2H). Owing to the very strong paramagnetic effect of terbium, it was not possible to determine the multiplicities of the signals.

Elemental analysis: calculated (found) for [Tb(TPDTZ)$_2$]NHEt$_3$.4.5H$_2$O0.15NHEt$_3$Otf:
C: 44.4 (44.22%)
H: 4.11% (3.63%)
N: 29.09% (29.08%)
X-Ray Diffraction:
Monoclinic crystalline system
Space group C2/c
Cell Parameters:
a=16.719(4) Å α=90°
b=18.270(4) Å β=93.225(6)°
c=14.453(3) Å γ=90°
R indices (all data) R1=0.0488

1.4. Synthesis of a Complex of TPDTZ and Neodymium

A suspension of 94.49 mg (0.256 mmol) of TPDTZ in 5 ml of methanol is treated with 71.3 μL of TEA and subjected to ultrasound. Then 75.7 mg of neodymium triflate in 1 ml of methanol are added. The resulting opalescent solution is filtered and the filtrate is left at ambient temperature to crystallize. The crystals thus formed are recovered by filtration, washed with a small volume of methanol and then of ether, and dried in the air.

Figure 3:
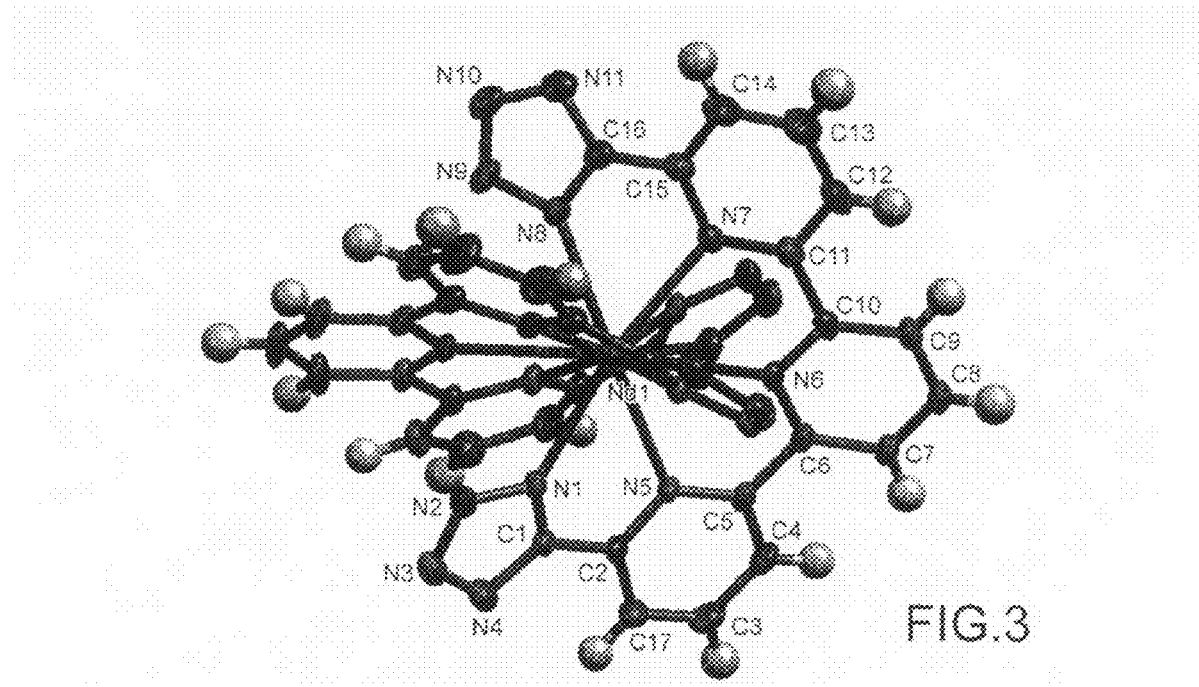
FIG. 3 shows the structure of a complex of neodymium, according to the invention, as resolved by X-ray diffraction.

This gives 51.9 mg of the complex whose structure, as resolved by X-ray diffraction, is shown in FIG. 3, in the form of white crystals (yield: 41.3%).

$^1$H NMR (400 MHz, MeOD) δ ppm: 16.18 (d, J=6.3 Hz, 2H), 14.99 (broad t, 1H), 11.37 (d, J=7.07 Hz, 2H), 5.84 (broad t, 2H), 3.11 (q, J=7.30, 7.30, 7.28 Hz, 3H), 2.06 (d, J=6.45 Hz, 2H), 1.22 (t, J=7.30, 7.30 Hz, 4.5H)

X-Ray Diffraction:
Monoclinic crystalline system
Space group C2/c
Cell Parameters:
a=16.901(4) Å α=90°
b=18.198(5) Å β=93.225(6)°
c=14.395(4) Å γ=90°
R indices (all data) R1=0.0623

EXAMPLE 2

Complex of 2,2'-6',2''-terpyridine-4'-(p-bromophenyl)-6,6''-ditetrazole and europium 2.1. Synthesis of 2,2'-6',2''-terpyridine-4'-(p-bromophenyl)-6, 6''-ditetrazole The title compound, referred to hereinafter as TPDTZPB, which corresponds to the compound of particular formula (II-b) shown above, is synthesized starting from [2,2'-6',2''-terpyridine]-4'-(p-bromo-phenyl)-6,6''-dicarbonitrile, referred to hereinafter as compound 2, in accordance with the following reaction scheme:

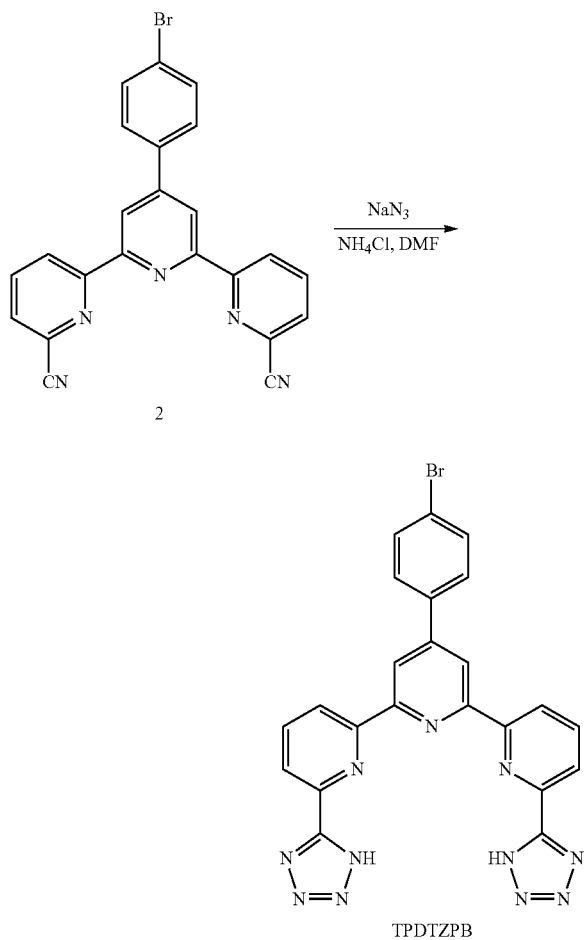 [SMILES: N#Cc1cccc(-c2cc(-c3ccc(Br)cc3)cc(-c3cccc(C#N)n3)n2)n1 ; Brc1ccc(-c2cc(-c3cccc(-c4nnn[nH]4)n3)nc(-c3cccc(-c4nnn[nH]4)n3)c2)cc1 ; "NaN3"]

Synthesis of Compound 2

Compound 2 is synthesized as described by Hovinen et al., *Organic Letters* 2001, 3, 2473-2476 [10].

Synthesis of TPDTZPB

A mixture of 435 mg (0.99 mmol) of compound 2, 325 mg (5 mmol) of NaN$_3$ and 267 mg (5 mmol) of NH$_4$Cl in 20 ml of anhydrous DMF is reacted under argon at 130° C. for 20 hours. After cooling, a precipitate is recovered by filtration, and is treated with dilute hydrochloric acid, stirred for one hour and refrigerated. Filtration, washing with cold water and drying under vacuum give 454 mg of TPDTZPB in the form of a bright yellow powder (yield: 87%).

The yield can be improved by subjecting the residue, after evaporation of the DMF, to a treatment with dilute HCl similar to that applied to the precipitate.

$^1$H NMR (200 MHz, DMSO) δ ppm: 9.04 (s, 2H), 8.79 (dd, J=7.18, 1.53 Hz, 2H), 8.30-8.17 (m, 4H), 8.05 (d, J=8.54 Hz, 2H), 7.86 (d, J=8.40 Hz, 2H), 3.86 (broad)

$^{13}$C NMR (50 MHz, DMSO) δ ppm: 156.62, 154.89, 148.60, 145.56, 138.96, 136.42, 132.09, 129.32, 123.12, 122.52, 121.84, 118.73.

2.2. Synthesis of the Complex of TPDTZPB and Europium

A suspension of 90.96 mg (0.1735 mmol) of TPDTZPB in 5 ml of methanol is admixed with 48.36 μl of TEA and then with 51.97 mg of europium triflate, giving an opalescent solution. Heating causes the opalescence to disappear, and a fine crystalline precipitate begins to form. The solution is left at ambient temperature overnight to crystallize. The resulting product is isolated by filtration, washed with a small volume of ethanol and dried in the air.

Figure 4:
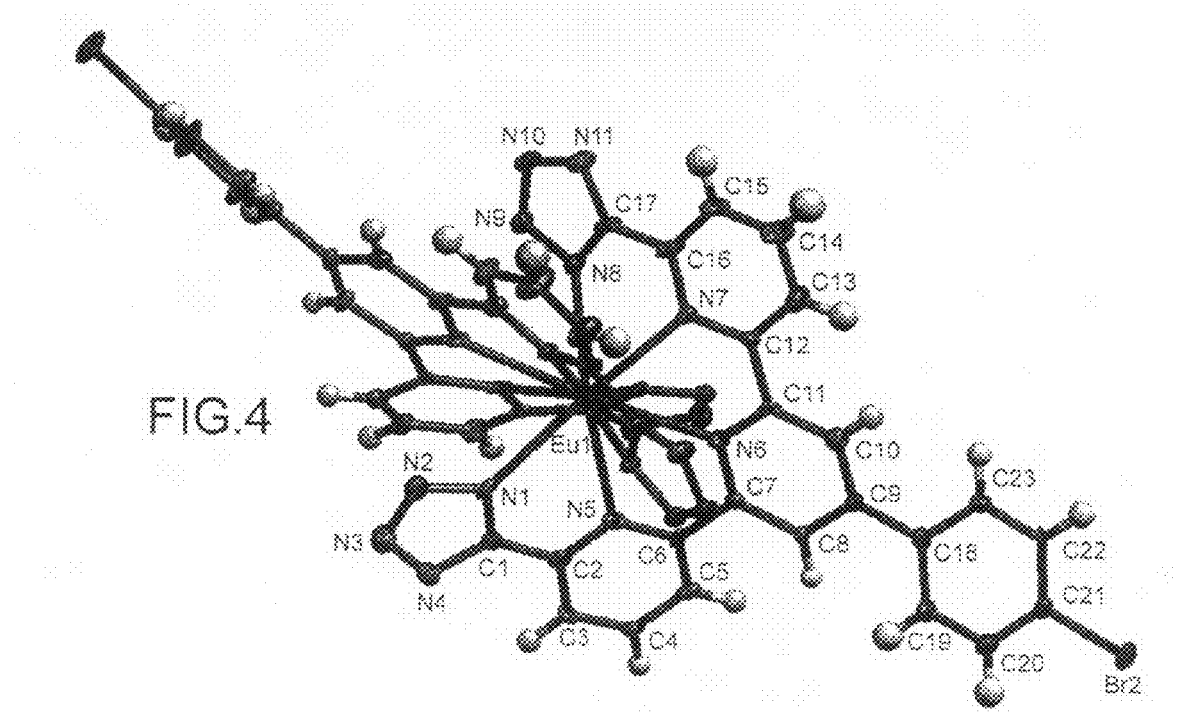
FIG. 4 shows the structure of a second complex of europium, according to the invention, as resolved by X-ray diffraction.

This gives 87.8 mg of the complex whose structure, as resolved by X-ray diffraction, is shown in FIG. 4, in the form of yellowish white crystals (yield: 77.9%).

$^1$H NMR (400 MHz, MeOD) δ ppm: 15.70 (d, J=7.98 Hz, 2H), 12.27 (t, J=7.89, 7.89 Hz, 2H), 6.06 (d, J=8.94 Hz, 2H), 5.40 (d, J=7.79 Hz, 2H), 4.08 (d, J=9.03 Hz, 2H), 3.17 (q, J=7.32, 7.32, 7.31 Hz, 3H), 1.28 (t, J=7.31, 7.31 Hz, 4.5H), −0.30 (s, 2H).

Elemental analysis: calculated (found) for [Eu(TPDTZPB)$_2$]NHEt$_3$.1.25MeOH.2.8H$_2$O:
C: 46.04% (46.03%)
H: 3.67% (3.26%)
N: 23.19% (23.15%)

X-Ray Diffraction:
Monoclinic crystalline system
Space group C2/c
Cell Parameters:
a=22.628(10) Å α=90°
b=19.032(8) Å β=107.356(7)°
c=14.977(7) Å γ=90°
R indices (all data) R1=0.1025

EXAMPLE 3

Complexes of 4'-(5-bromo-2-thienyl)-2,2'-6',2''-terpyridine-6,6''-ditetrazole and various lanthanides (europium and neodymium)

3.1. Synthesis of 4'-(5-bromo-2-thienyl)-2,2'-6',2''-terpyridine-6,6''-ditetrazole The title compound, referred to hereinafter as TPDTZTB, which corresponds to the compound of particular formula (II-a) shown above, is synthesized starting from 4'-(5-bromo- 2-thienyl)-2,2'-6',2''-terpyridine, referred to hereinafter as compound 3, in accordance with the following reaction scheme:

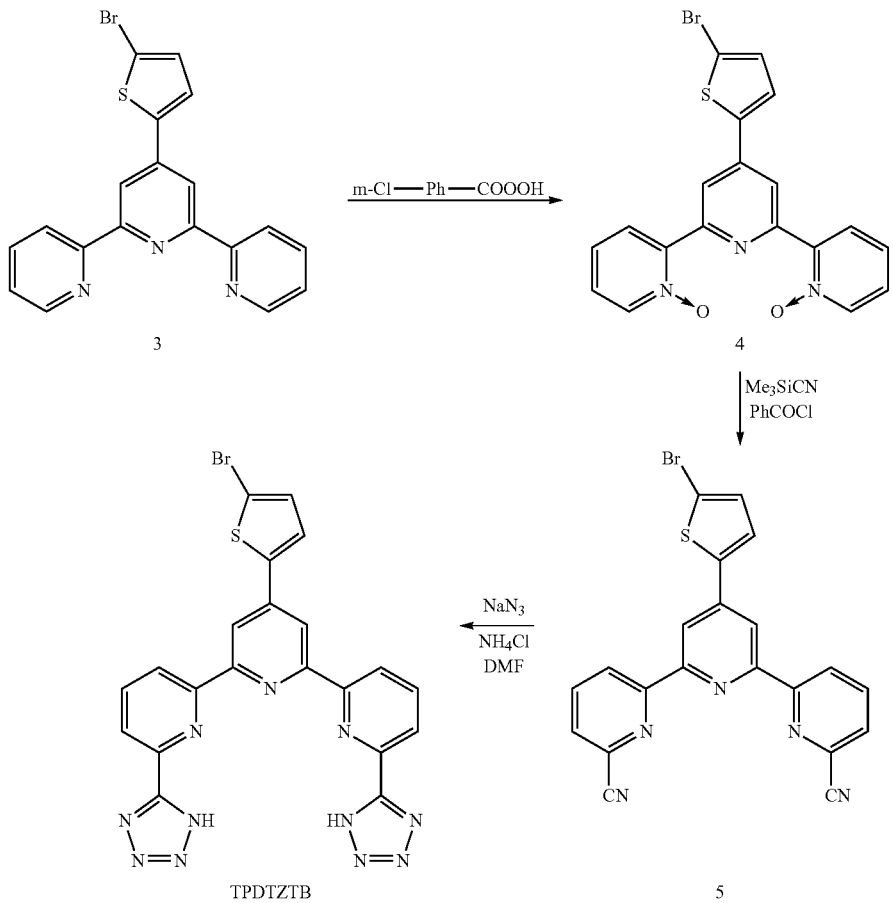

Synthesis of Compound 3

Compound 3 is synthesized as described by Ferraudi, Moya and colleagues in López et al., *Inorganica Chimica Acta* 2004, 357, 3525-3531 [11].

Synthesis of 4'-(5-bromo-2-thienyl)-2,2'-6',2''-terpyridine 1,1''-dioxide or compound 4

A suspension of 5.62 g (22.8 mmol) of 70% 3-chloroperbenzoic acid in dichloromethane ($CH_2Cl_2$) is added slowly to a solution containing 2.40 g (6.09 mmol) of compound 3 in 50 ml of $CH_2Cl_2$. The mixture is stirred for 18 hours at ambient temperature. Then it is washed with 10% sodium carbonate solution, dried over $Na_2SO_4$ and concentrated. Purification by chromatography on alumina with ethyl acetate and ethanol gives 1.55 g of a white powder (yield: 60%).

$^1$H NMR (200 MHz, $CDCl_3$) δ ppm: 9.14 (s, 2H), 8.35 (dd, J=6.06, 1.32 Hz, 2H), 8.23 (dd, J=7.75, 2.37 Hz, 2H), 7.44 (d, J=3.40 Hz, 1H), 7.36 (td, J=7.70, 1.36 Hz, 2H), 7.32 (td, J=7.50, 2.30 Hz, 2H), 7.10 (d, J=3.94, 1H)

Synthesis of 4'-(5-bromo-2-thienyl)-2,2'-6',2''-terpyridine-6,6''-dicarbonitrile or compound 5

A solution of 3 g (7.04 mmol) of compound 4 and 7 g (70 mmol) of cyanotrimethylsilane ($Me_3SiCN$) in 100 ml of $CH_2Cl_2$ is stirred at ambient temperature for 20 minutes. Then 3.95 g (28 mmol) of benzoyl chloride are added dropwise and the resulting solution is stirred at ambient temperature for 20 hours. Filtration gives a precipitate, which is washed with water and with methanol and dried.

This gives 2.00 g of compound 5 in the form of a yellowish white solid (yield: 64%).

$^1$H NMR (200 MHz, DMSO, 80° C.) δ ppm: 8.80 (dd, J=8.11, 0.95 Hz, 2H), 8.59 (s, 2H), 8.01 (t, J=7.87, 7.87 Hz, 2H), 7.76 (dd, J=7.60, 0.96 Hz, 2H), 7.55 (d, J=3.95 Hz, 1H), 7.16 (d, J=3.94 Hz, 1H)

Synthesis of TPDTZTB

A mixture of 633 mg (1.425 mmol) of compound 5, 463 mg (7.12 mmol) of $NaN_3$ and 381 mg (7.12 mmol) of $NH_4Cl$ in 15 ml of anhydrous DMF is stirred under argon at 140° C. for 20 hours. After cooling, a precipitate is recovered by filtration and is treated with dilute hydrochloric acid, with stirring, for 1 hour. The organic phase is evaporated and the residue is taken up in dilute HCl, subjected to ultrasound and stirred for 1 hour. The acidic suspensions are combined, filtered, washed with cold water and dried under vacuum.

This gives 630 mg of TPDTZTB in the form of a brown-yellow powder (yield: 90%).

$^1$H NMR (200 MHz, DMSO) δ ppm: 8.86 (s, 2H), 8.77 (d, J=7.18 Hz, 2H), 8.30 (d, J=6.91 Hz, 2H), 8.22 (t, J=7.60 Hz, 2H), 7.94 (d, J=3.88 Hz, 1H), 7.47 (d, J=3.80 Hz, 1H)

$^{13}$C NMR (50 MHz, DMSO) δ ppm: 154.84, 154.46, 143.02, 142.38, 142.02, 139.36, 131.91, 127.98, 122.91, 122.83, 116.90, 114.46

Figure 5:
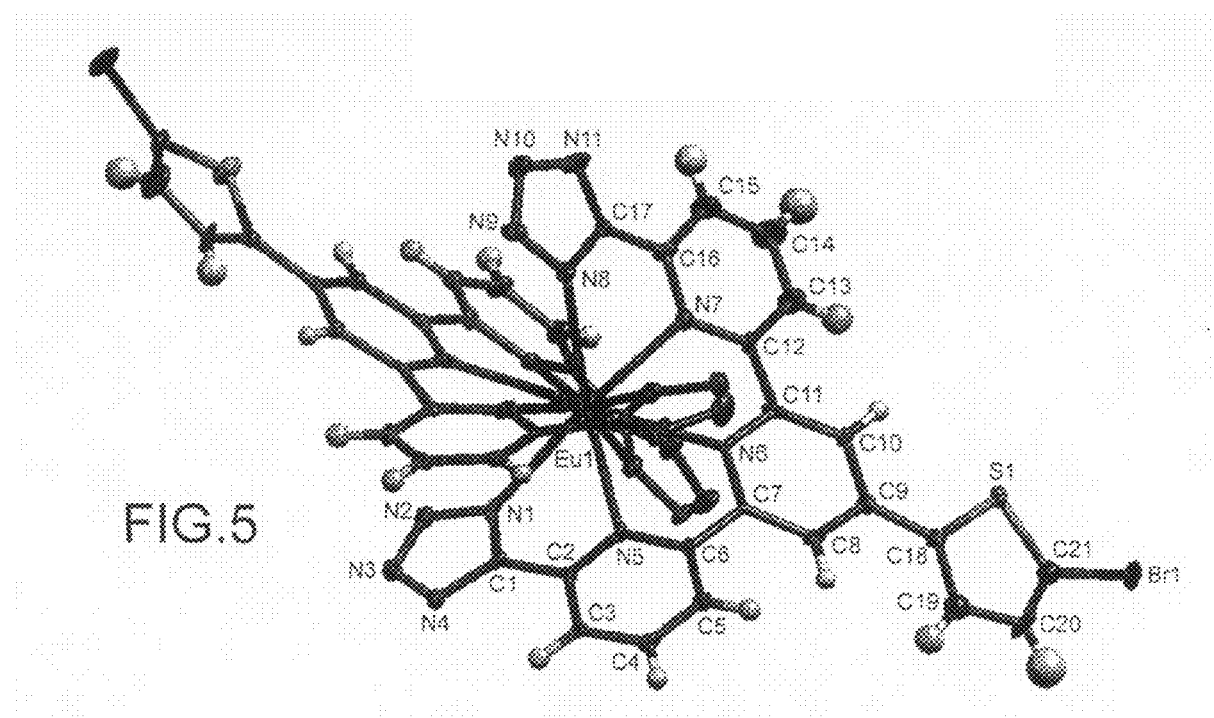
FIG. 5 shows the structure of a third complex of europium, according to the invention, as resolved by X-ray diffraction.

3.2. Synthesis Complex of TPDTZTB and Europium 98.03 mg (0.185 mmol) of TPDTZTB in suspension in 5 ml of methanol are treated with 51.5 µL of TEA and subjected to ultrasound. Then 55.4 mg of europium triflate in 2 ml of methanol are added. An orange-yellow precipitate is formed immediately, and is redissolved completely in approximately 3 minutes by heating. The resulting solution is filtered and left overnight at ambient temperature. This gives fine crystals, which are recovered by filtration and washed with a small volume of ethanol, acetonitrile and isopropyl ether. Air drying gives 77 mg of the complex whose structure, as dissolved by X-ray diffraction, is shown in FIG. 5, in the form of a yellow product (yield: 64%).

$^{1}$H NMR (400 MHz, MeOD) δ ppm: 15.74 (d, J=8.21 Hz, 2H), 12.29 (t, J=8.03, 8.03 Hz, 2H), 5.62 (d, J=4.37 Hz, 1H), 5.39 (d, J=7.81 Hz, 2H), 4.20 (d, J=4.32 Hz, 1H), 3.16 (q, J=7.27, 7.27, 7.25 Hz, 3H), 1.27 (t, J=7.32, 7.32 Hz, 4.5H), −0.38 (s, 2H)

Elemental analysis: calculated (found) for [Eu(TPDTZTB)$_2$]NHEt$_3$.1MeOH.1.5H$_2$O:
 C: 42.96% (42.83%)
 H: 3.16% (2.99%)
 N: 23.52% (23.46%)

X-Ray Diffraction:
 Monoclinic crystalline system
 Space group P2(1)/c
 Cell Parameters:
 a=20.964(8) Å α=90°
 b=19.285(8) Å β=105.007(7)°
 c=14.278(5) Å γ=90°
 R indices (all data) R1=0.1103

3.3. Synthesis of a Complex of TPDTZTB and Neodymium 94.48 mg (0.178 mmol) of TPDTZTB in suspension in 3 ml of methanol are treated with 50 µL of TEA and subjected to ultrasound. Then 52.64 mg of neodymium triflate in 2 ml of methanol are added. An orange-yellow precipitate is formed immediately, and is redissolved completely in approximately 1 minute by heating. The resulting solution is filtered and left overnight at ambient temperature. This gives fine crystals, which are recovered by filtration and washed with a small volume of ethanol, acetonitrile and isopropyl ether.

This gives 67.8 mg of a yellow product (yield: 58%).

$^{1}$H NMR (400 MHz, MeOD) δ ppm: 16.51 (s, 2H), 11.70 (d, J=7.46 Hz, 2H), 11.53 (d, J=3.20 Hz, 1H), 8.97 (d, J=3.25 Hz, 1H), 5.83 (t, J=6.10, 6.10 Hz, 2H), 3.16 (q, J=7.32, 7.32, 7.31 Hz, 3H), 1.91 (d, J=6.54 Hz, 2H), 1.26 (t, J=7.31, 7.31 Hz, 4.5H)

Elemental analysis: calculated (found) for [Nd(TPDTZTB)$_2$]NHEt$_3$.1MeOH:
 C: 44.08% (44.18%)
 H: 3.02% (2.96%)
 N: 24.13% (24.11%)

EXAMPLE 4

Complexes of 1,4,7-tris[6-tetrazolylpyridin-2-yl) methyl]-1,4,7-triazacyclononane and various lanthanides (europium, terbium, neodymium, gadolinium and ytterbium)

4.1. Synthesis of 1,4,7-tris[6-tetrazolylpyridin-2-yl)methyl]-1,4,7-triazacyclononane The title compound, referred to hereinafter as H$_3$TTPTCN, which corresponds to the compound of particular formula (II-i) shown above, is synthesized starting from 2-cyano-6-methylpyridine, referred to hereinafter as compound 6, in accordance with the following reaction scheme:

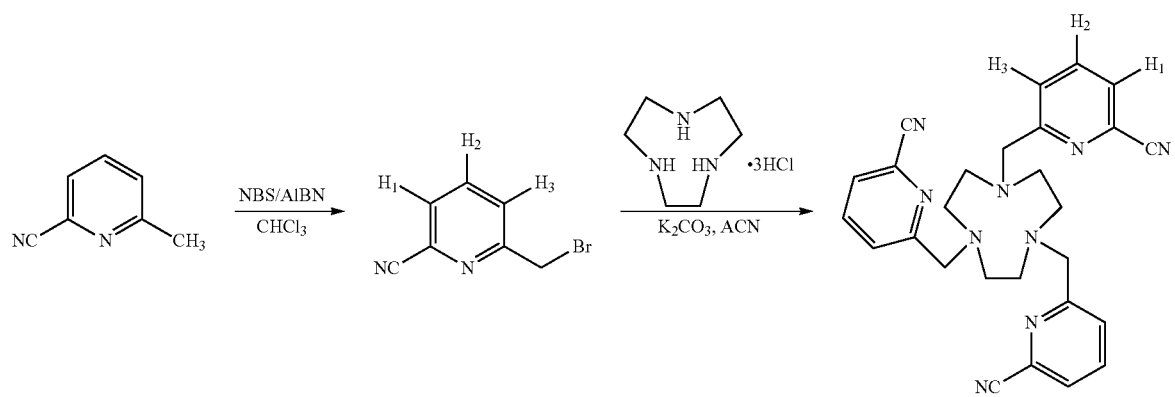

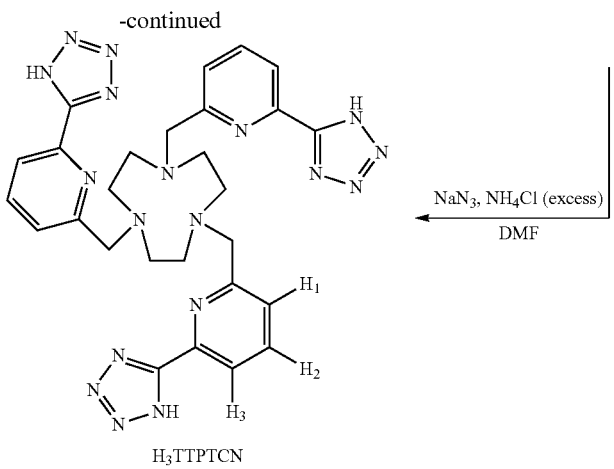

H₃TTPTCN

Compound 6 is available commercially.

Synthesis of 2-bromomethyl-6-cyanopyridine or compound 7

A solution of 400 mg (3.39 mmol) of 2-cyano-6-methylpyridine in 12 ml of CHCl₃ is admixed with 723 mg (4.06 mmol) of N-bromosuccinimide (NBS) and 28 mg (0.17 mmol) of azobisisobutyronitrile (AIBN). The resulting orange-brown suspension is refluxed and irradiated with a UV lamp for 4 hours (the reaction is monitored by TLC on silica plates, using $CH_2Cl_2$ as eluant–Rf=0.43). The reaction mixture is cooled to ambient temperature and the solvent is evaporated under reduced pressure. The crude product is purified by chromatography on a silica gel column, using a continuous gradient from an 85/15 v/v $CH_2Cl_2$/heptane mixture to pure $CH_2Cl_2$ as eluant.

This gives 290 mg of compound 7 in the form of a white microcrystalline powder (yield: 43%).

$^1$H NMR (200 MHz, CDCl₃) δ ppm: 4.55 (s, 2H, pyCH₂Br), 7.63 (dd, J=7.63, 1.27 Hz, 1H, H₃), 7.70 (dd, J=7.95, 1.27 Hz, 1H, H₁), 7.87 (t, J=7.95 Hz, 7.63 Hz, 1H, H₂).

Elemental Analysis: Calculated (Found):
C: 42.67% (42.80%)
H: 2.56% (2.57%)
N: 14.22% (14.53%)

Synthesis of 1,4,7-tris[6-cyanopyridin-2-yl)methyl]-1,4,7-triazacyclononane or compound 8

A suspension of 238 mg (1 mmol) of 1,4,7-triazacyclononane trishydrochloride in 30 ml of anhydrous acetonitrile (CAN) is admixed in succession with 853 mg (6.2 mmol) of K₂CO₃ and 610 mg (3.1 mmol) of compound 7 under an argon atmosphere. The reaction medium is refluxed for 6 hours. After filtration to remove the inorganic salts, and evaporation of the solvent, the crude product is purified by chromatography on an alumina column (activity III) using pure $CH_2Cl_2$ and then a 99/1 v/v $CH_2Cl_2$/EtOH mixture as eluant.

This gives 339 mg of compound 8 in the form of a brown-yellow oil (yield: 71%).

$^1$H NMR (200 MHz, CDCl₃) δ ppm: 2.91 (s, 12H, N(CH₂)₂N), 3.90 (s, 6H, pyCH₂N), 7.63 (dd, J=7.31, 1.27 Hz, 3H, H₃), 7.77 (d, J=7.00 Hz, 3H, H₁), 7.86 (d, 7.63 Hz, 3H, H₂)

Synthesis of H₃TTPTCN

A suspension of 835 mg (12.8 mmol) of NaN₃ and 693 mg (12.9 mmol) of anhydrous NH₄Cl in 4 ml of DMF is admixed with a solution of 409 mg (0.85 ml) of compound 8 under an argon atmosphere. The reaction mixture is refluxed overnight. The inorganic salts are removed by filtration. The orange filtrate is set aside and the salts are washed with 4×10 ml of dimethyl sulphoxide (DMSO). The pale yellow DMSO fraction is evaporated under reduced pressure and 5 ml of dilute hydrochloric acid (1 M) are added to the residue, leading to the formation of a precipitate. This precipitate is recovered by filtration, washed with water (2×2 ml) and then with ethanol (2×2 ml) and dried under vacuum.

This gives 280 mg of H₃TTPTCN in the form of a beige powder (yield: 54%).

$^1$H NMR (200 MHz, D₂O) δ ppm: 2.49 (s, 12H, N(CH₂)₂N), 3.46 (s, 6H, pyCH₂N), 7.04 (d, J=7.73 Hz, 3H, H₃), 7.46 (t, J=7.70, 7.60 Hz, 3H, H₁), 7.57 (d, J=7.57, 3H, H₁).

$^1$H NMR (200 MHz, DMSO) δ ppm: 7.60 (d, 3H, J=7.4 Hz), 7.49 (t, 3H, J=7.8, 7.4 Hz), 7.04 (d, 3H, J=7.8 Hz), 3.47 (s, 6H), 2.48 (s, 12H)

ES-MS m/z (%): 607.14 (100) [M+H]⁺, 623.3 (20) [M+2H]²⁺.

Elemental analysis: calculated (found) for H₃TTPTCN.2.5H₂O.2HCl:
C: 44.75% (44.80%)
H: 5.15% (5.11%)
N: 34.79% (34.34%)

4.2. Synthesis of Complexes of H₃TTPTCN and Lanthanides

A solution of 29.6 mg (0.05 mmol) of europium triflate in 1 ml of water is admixed with a solution of 36 mg (0.05 mmol) of H₃TTPTCN in 2 ml of water in which the pH is adjusted to 7 by addition of aqueous NaOH (1 M then 0.1 M). A white precipitate forms immediately. The suspension is stirred for 15 minutes and then the precipitate is recovered by filtration and dried under vacuum.

Figure 6:
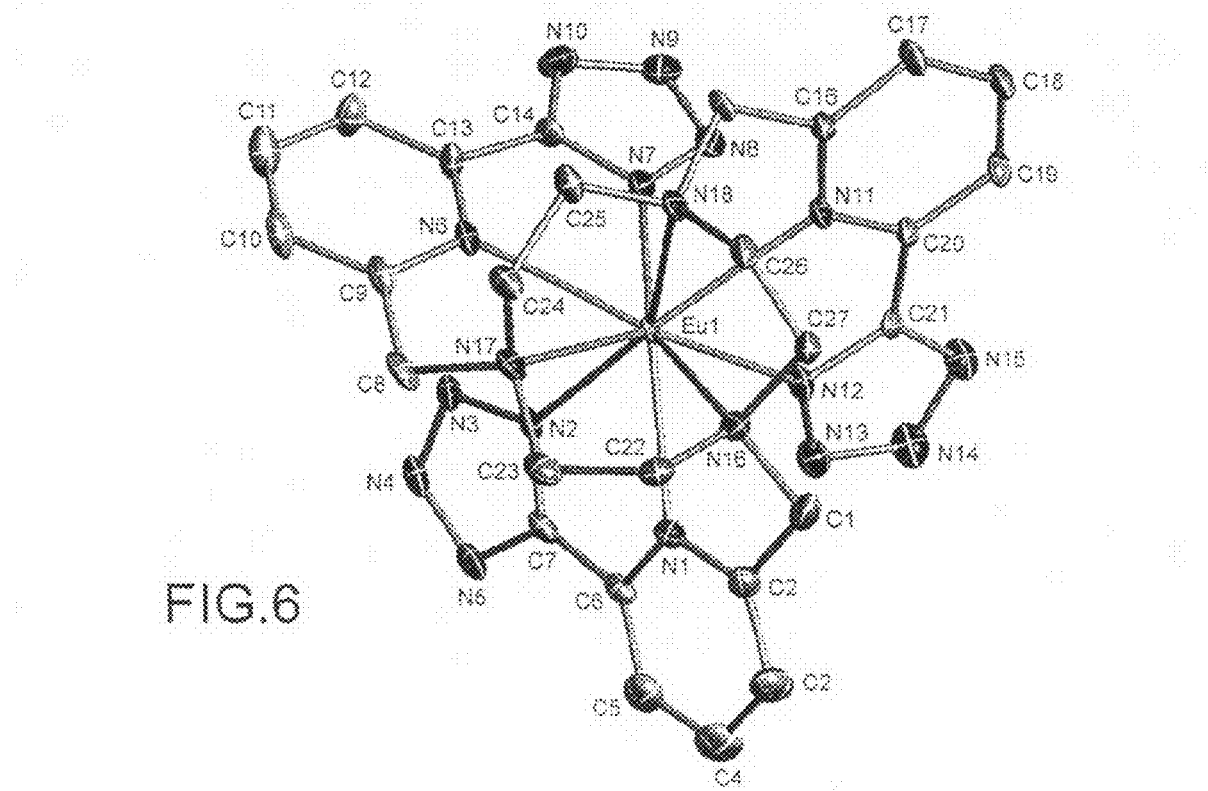
FIG. 6 shows the structure of a fourth complex of europium, according to the invention, as resolved by X-ray diffraction.

The complex is isolated in the form of [Eu(TTPTCN)].5.7H₂O (yield: 37%). Its structure, as resolved by X-ray diffraction, is shown in FIG. 6.

Elemental analysis: calculated (found):
C: 37.78% (38.23%)
H: 4.51% (4.49%)
N: 29.38% (28.95%)

4.3. Synthesis of a Complex of H₃TTPTCN and Terbium

A solution of 30.1 mg (0.05 mmol) of terbium triflate in 1 ml of water is admixed with a solution of 36 mg (0.05 mmol) of H₃TTPTCN in 2 ml of water in which the pH is adjusted to 7 by addition of an aqueous NaOH solution. The subsequent procedure is as described in section 4.2 above.

In this way a complex is isolated: [Tb(TTPTCN)].H₂O (yield: 55%).
Elemental analysis: calculated (found):
C: 41.55% (41.54%)
H: 3.74% (3.74%)
N: 32.30% (32.08%)

4.4. Synthesis of a Complex of H₃TTPTCN and Neodymium

A solution of 29.6 mg (0.05 mmol) of neodymium triflate in 1 ml of water is admixed with a solution of 36.2 mg (0.05 mmol) of H₃TTPTCN in 2 ml of water in which the pH is adjusted to 7 by addition of an aqueous NaOH solution. The subsequent procedure is as described in section 4.2 above.

In this way a complex is isolated: [Nd(TTPTCN)].5H₂O (yield: 42%).
Elemental analysis: calculated (found):
C: 38.70% (39.00%)
H: 4.45% (4.32%)
N: 30.09% (29.65%)

4.5. Synthesis of a Complex of H₃TTPTCN and Gadolinium

A solution of 12.1 mg (0.02 mmol) of gadolinium triflate in 1 ml of water is admixed with a solution of 12.4 mg (0.02 mmol) of H₃TTPTCN in 1 ml of water in which the pH is adjusted to 7 by addition of an aqueous NaOH solution. Then approximately 7 ml of water are added, to give a clear solution, which is subsequently left to evaporate, producing crystals.

In this way a complex is isolated: [Gd(TTPTCN)].6H₂O.

4.6. Synthesis of a Complex of H₃TTPTCN and Ytterbium

A solution of 30.5 mg (0.05 mmol) of ytterbium triflate in 1 ml of water is admixed with a solution of 36 mg (0.05 mmol) of H₃TTPTCN in 2 ml of water in which the pH is adjusted to 7 by addition of an aqueous NaOH solution. The subsequent procedure is as described in section 4.2 above.

In this way a complex is isolated: [Yb(TTPTCN)].6.5H₂O (yield: 30%).
Elemental analysis: calculated (found):
C: 33.55% (33.69%)
H: 4.38% (4.37%)
N: 26.08% (25.61%)

EXAMPLE 5

Photophysical Properties of Lanthanide Complexes According to the Invention

5.1. In Solution

The photophysical properties exhibited in solution by the europium complex synthesized in Example 1 above (whose ligand is 2,2-6',2"-terpyridine-6,6"-ditetrazole or TPDTZ) were studied and compared with those of a europium complex whose ligand is 2,2'-6',2"-terpyridine-6,6"-dicarboxylate, referred to hereinafter as TPDC, of formula:

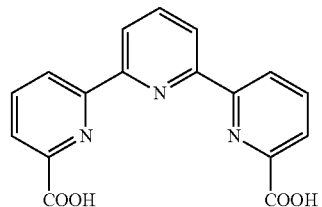 [SMILES: O=C(O)c1cccc(-c2cccc(-c3cccc(C(=O)O)n3)n2)n1]

The photophysical properties in solution of the europium complex based on TPDC were reported by Latva et al. in reference [1].

Table 1 below shows the triplet states, lifetimes and quantum yields exhibited in solution by the complex according to the invention and the complex studied by Latva et al.

TABLE 1

| Complex | According to the invention (ligand = TPDTZ) | Studied by Latva et al. (ligand = TPDC) |
| --- | --- | --- |
| Triplet state nm (cm⁻¹) | 451 (22173) | 438 (22850) |
| Lifetime (ms) | 3.34 | 0.31-0.82 |
| Quantum yield (%) | 28.0 | 11.0 |

This table shows that the quantum yield of the europium complex according to the invention in solution is markedly higher than that reported by Latva et al. for the corresponding complex based on TPDC.

5.2. In the Solid State

The photophysical properties exhibited in the solid state by the europium and neodymium complexes synthesized in Examples 1 and 3 above (whose ligands are, respectively, 2,2'-6',2"-terpyridine-6,6"-ditetrazole, or TPDTZ, and 4'-(5-bromo-2-thienyl)-2,2'-6',2"-terpyridine-6,6"-ditetrazole, or TPDTZTB), and also by the europium complex synthesized in Example 2 above (whose ligand is 2,2'-6',2"-terpyridine-4'-(p-bromophenyl)-6,6"-ditetrazole, or TPDTZPB), were studied and compared with one another.

Table 2 below shows the triplet states, the excitation maxima, the lifetimes and the quantum yields of these complexes in the solid state.

TABLE 2

| Ligand | TPDTZ | | TPDTZPB | TPDTZTB |
| --- | --- | --- | --- | --- |
| Triplet state nm (cm⁻¹) | 451 (22173) | | 446 (22422) | 542 (18450) |
| Complexed metal | Eu | Nd | Eu | Nd |
| Excitation maximum (nm) | 369 | 370 | 367 | 378 |
| Lifetime (ms) | 2.50 | — | 2.47 | — |
| Quantum yield (%) | 35.3 (2) | 0.22 (1) | 29.4 (6) | 0.29 (2) |

This table shows that the quantum yields of the europium complexes according to the invention in the solid state are high, which means that the terpyridine-tetrazole ligands according to the invention are capable of sensitizing europium very effectively.

These ligands are also capable of sensitizing neodymium effectively by comparison with the ligands of the prior art, since the quantum yields obtained for the complexes of this lanthanide according to the invention are at least twice as high as those typically reported in the literature for the complexes of the same lanthanide.

Moreover, it may be noted that the lifetime value obtained for the complex of TPDTZ and europium in the solid state is close to that obtained for this same complex in solution (see Table 1), which suggests very high stability of the complexes according to the invention.

Also tested were the photophysical properties exhibited in the solid state by the europium and terbium complexes synthesized in Example 4 above, whose ligand is 1,4,7-tris[6-tetrazolylpyridin-2-yl)methyl]-1,4,7-triazacyclonoriane, or $H_3$TTPTCN.

The results of these tests, in terms of quantum yield and lifetime, are shown in Table 3 below.

TABLE 3

| Complexed metal | Eu | Tb |
| --- | --- | --- |
| Lifetime (ms) | 1.13 (4) | 1.56 (6) |
| Quantum yield (%) | 19.8 (4) | 56.1 (3) |

Here again, the europium and terbium complexes according to the invention are observed to exhibit very high quantum yields in the solid state. For comparison, the quantum yield obtained for a europium complex prepared from a carboxylate analogue of $H_3$TTPTCN, in the solid state, is only 6%.

Figure 7:
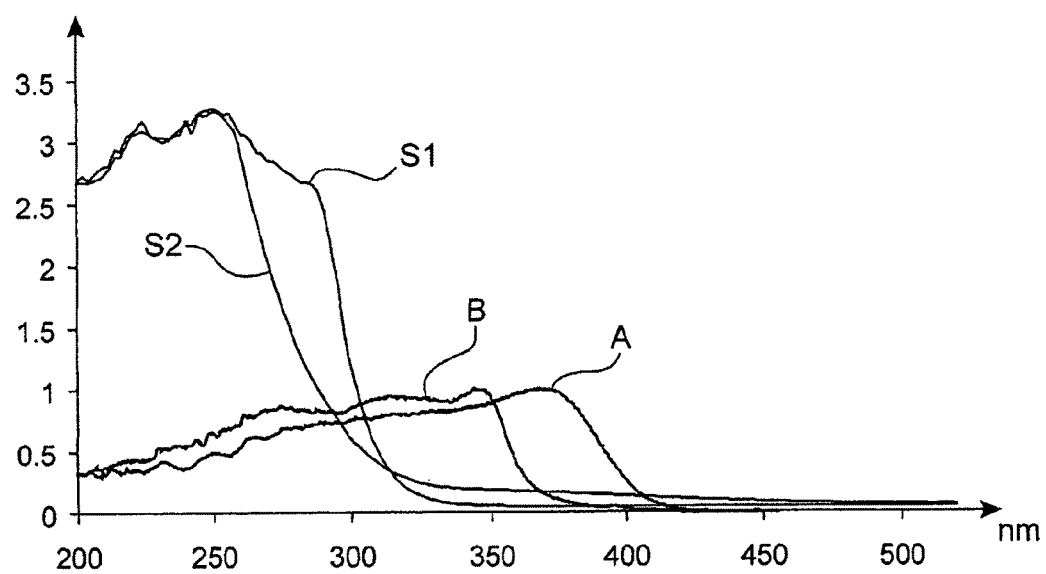
FIG. 7 shows the electronic excitation spectra of a europium complex according to the invention (curve A) and of a europium complex of the prior art (curve B) and also the absorption spectra of a glass substrate (curve S1) and of an ITO substrate (curve S2).

Moreover, as shown by FIG. 7, which shows the electronic excitation spectra exhibited in the solid state by the europium complex synthesized in Example 1 above (curve A) and the corresponding complex based on TPDC (curve B), and also the absorption spectra of a glass substrate (curve S1) and of an ITO substrate (curve S2), the non-overlap zone of these spectra is markedly wider in the case of the complex according to the invention.

This means that this complex can be excited with radiation that is less energetic than that required for the complex of the prior art, at 400 nm, for example, thereby significantly reducing the likelihood of causing the complex to degrade.

REFERENCES CITED

[1] Latva et al., *Journal of Luminescence* 1997, 75, 149-169
[2] Chatterton et al., *Angewandte Chemie*, international edition in English 2005, 44, 7595-7598
[3] Nonat et al., *Chemistry, a European Journal* 2006, 12, 7133-7150)
[4] Petoud et al., *Journal of the American Chemical Society* 2003, 125, 13324-13325
[5] Moore et al., *Inorganic Chemistry* 2007, 46, 5468-5470
[6] Vogtle et al., *ChemPhysChem* 2001, 2, 769-773
[7] Chauvin et al., *Spectroscopy Letters* 2004, 37, 517-532
[8] Mello et al., *Advanced Materials* 1997, 9, 230-232
[9] Mukkala et al., *Helvetica Chimica Acta* 1992, 75, 1621-1632
[10] Hovinen et al., *Organic Letters* 2001, 3, 2473-2476
[11] Lopez et al., *Inorganica Chimica Acta* 2004, 357, 3525-3531

The invention claimed is:

1. A process for complexing a lanthanide with an organic chromophore, comprising putting the lanthanide in contact with the organic chromophore to form a complex, the organic chromophore being a compound of formula (II):

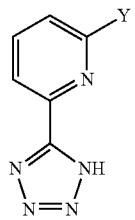

(II)

wherein:
either a group of formula:

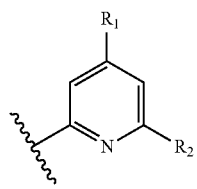

wherein:
$R_1$ is (a) a hydrogen atom; (b) a halogen atom; (c) a 5-membered aromatic ring or a 6-membered aromatic ring, the ring comprising one or more heteroatoms or one or more non-cyclic substituents; (d) a sequence of at least two 5-membered aromatic rings or a sequence of at least two 6-membered aromatic rings, the rings being bonded to one another by a covalent bond and at least one of the rings optionally comprising one or more heteroatoms or one or more non-cyclic substituents; or (e) a linear or branched $C_1$ to $C_{12}$ hydrocarbon group optionally comprising one or more heteroatoms; and $R_2$ is (a) a carboxylic acid group; (b) a 5-membered aromatic ring or a 6-membered aromatic ring, the ring optionally comprising one or more heteroatoms or one or more non-cyclic cyclic substituents; or (c) a 2-(1H-tetrazol-5-yl)pyridine unit;

or Y is (a) a non-aromatic ring optionally comprising one or more heteroatoms or one or more substituents; or (b) a group —$(CH_2)_p$—Z where p is an integer from 1 to 6 and Z is a non-aromatic ring, optionally comprising one or more heteroatoms or one or more substituents;

whereby the lanthanide is complexed with the organic chromophore.

2. The process of claim 1, wherein Y is a group of formula —$(CH_2)_p$—Z where p is 1 or 2 and Z is a 5-membered to 9-membered non-aromatic ring.

3. The process of claim 2, wherein Z is a 9-membered non-aromatic ring comprising 2 to 5 heteroatoms.

4. The process of claim 3, wherein Z is a triazacyclononane ring or a tetraazacyclononane ring.

5. The process of claim 1, wherein the compound comprises one of formulae (II-a) to (II-j):

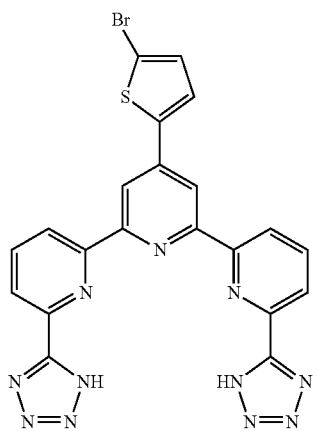
(II-a)
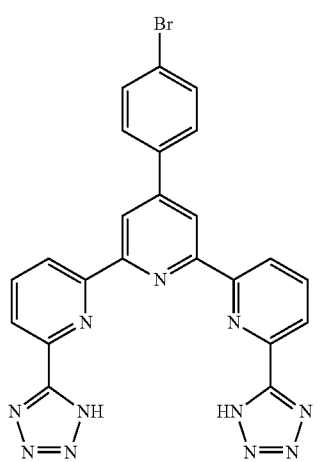
(II-b)
(II-c)
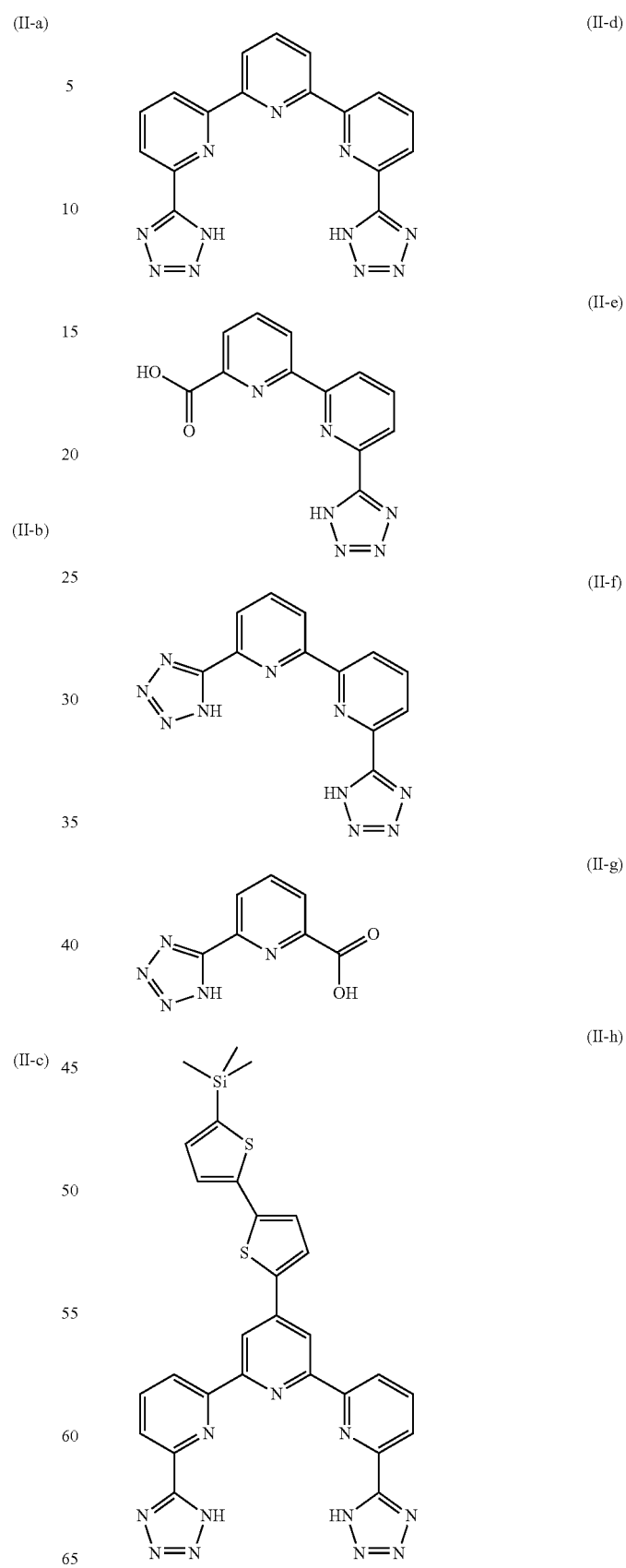

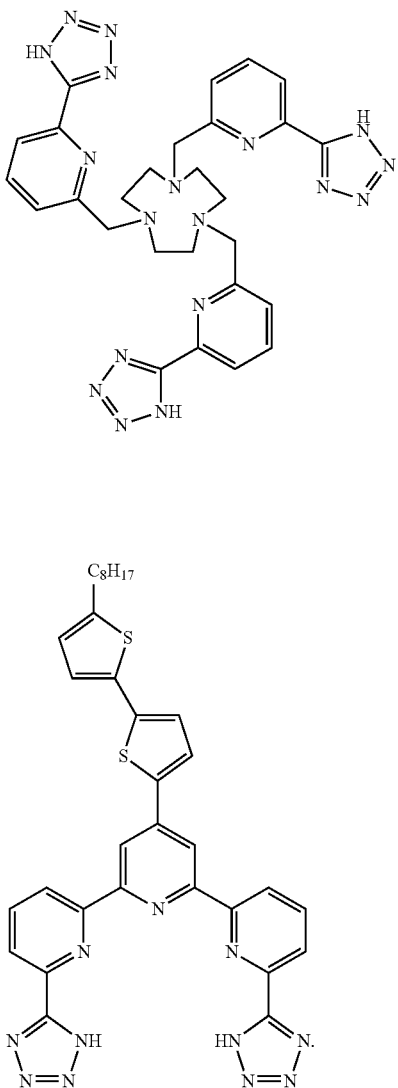

(II-i)

(II-j)

6. The process of claim 1, wherein the lanthanide is europium, terbium or neodymium.

7. A complex, comprising at least one compound of formula (II):

(II)

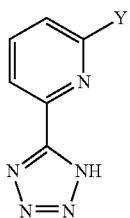

wherein:
n is an integer from 1 to 5; and
either Y is a group of formula:

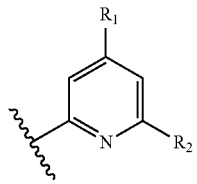

wherein $R_1$ is (a) a hydrogen atom; (b) a halogen atom; (c) a 5-membered aromatic ring or a 6-membered aromatic ring, the ring comprising one or more heteroatoms or one or more non-cyclic substituents; (d) a sequence of at least two 5-membered aromatic rings or a sequence of at least two 6-membered aromatic rings, the rings being bonded to one another by a covalent bond and at least one of the rings optionally comprising one or more heteroatoms or one or more non-cyclic substituents; or (e) a linear or branched $C_1$ to $C_{12}$ hydrocarbon group optionally comprising one or more heteroatoms; and $R_2$ is (a) a carboxylic acid group; (b) a 5-membered aromatic ring or a 6-membered aromatic ring, the ring optionally comprising one or more heteroatoms or one or more non-cyclic cyclic substituents; or (c) a 2-(1H-tetrazol-5-yl)pyridine unit;

or Y is (a) a non-aromatic ring optionally comprising one or more heteroatoms or one or more substituents or (b) a group —$(CH_2)_p$—Z where p is an integer from 1 to 6 and Z is a non-aromatic ring, optionally comprising one or more heteroatoms or one or more substituents;

and a lanthanide complexed with the compound.

8. The complex of claim 7, wherein Y is —$(CH_2)_p$—Z where p is 1 or 2 and Z is a 5-membered to 9-membered non-aromatic ring.

9. The complex of claim 8, wherein Z is a 9-membered non-aromatic ring comprising 2 to 5 hetero-atoms.

10. The complex of claim 9, wherein Z is a triazacyclononane ring or a tetraazacyclononane ring.

11. The complex of claim 7, wherein the compound comprises one of formulae (II-a) to (II-j):

(II-a)

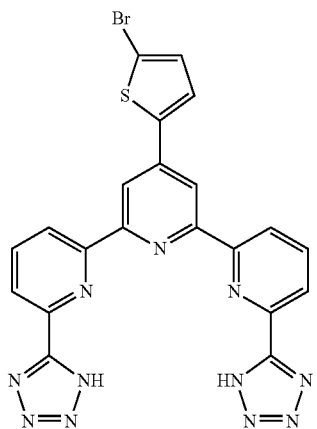

-continued
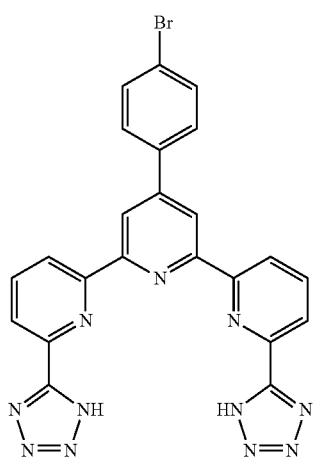
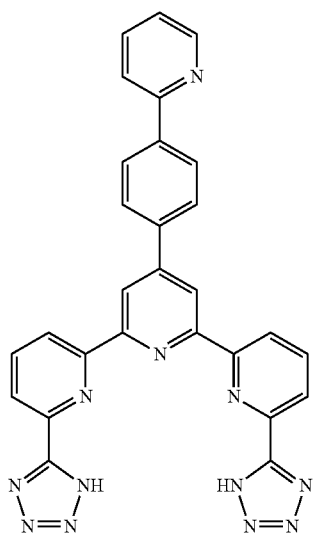
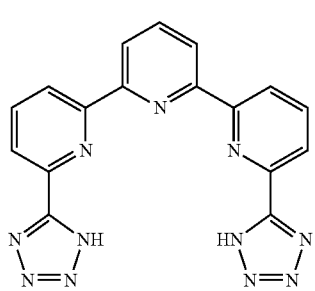
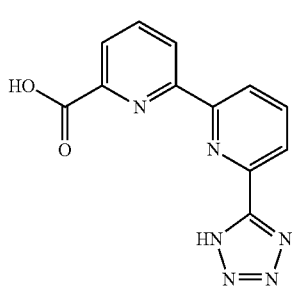
-continued
(II-b)
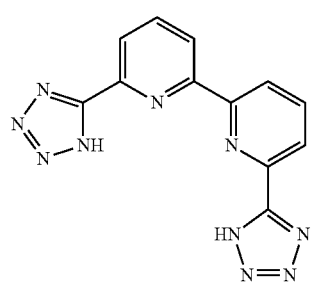
(II-c)
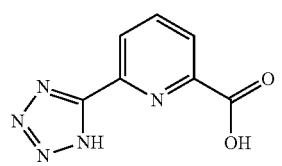
(II-d)
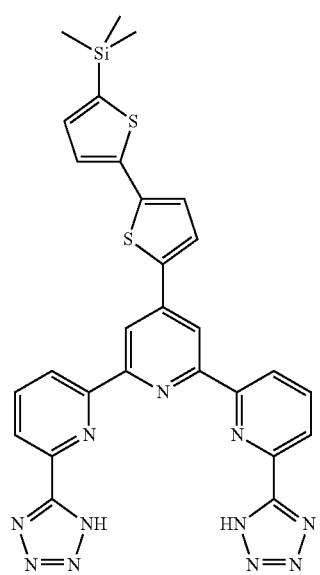
(II-e)
(II-f)
(II-g)
(II-h)
(II-i)
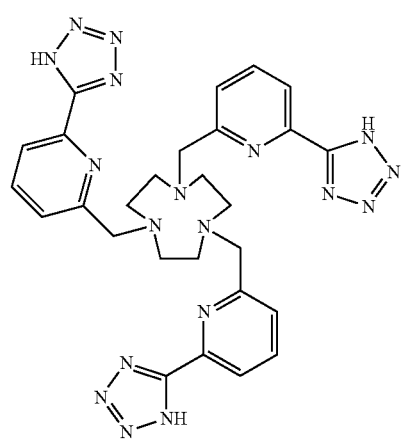

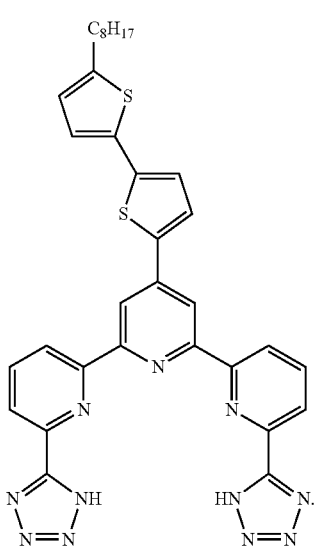
(II-j)
12. The complex of claim 7, wherein the lanthanide is selected from europium, terbium and neodymium.